United States Patent [19]

Brunner et al.

[11] 4,412,856
[45] Nov. 1, 1983

[54] HERBICIDAL HETEROCYCLIC AND SUBSTITUTED PHENYL PHENYLACETYLENE AMINES

[75] Inventors: Hans-Georg Brunner, Lausen; Rolf Schurter, Binningen; Henry Szczepanski, Rheinfelden, all of Switzerland

[73] Assignee: Ciba-Geigy Corporation, Ardsley, N.Y.

[21] Appl. No.: 266,264

[22] Filed: May 22, 1981

[30] Foreign Application Priority Data

May 31, 1980 [CH] Switzerland ............ 4232/80

[51] Int. Cl.³ .................. A01N 33/10; A01N 43/08; A01N 43/10; A01N 43/54; A01N 43/66; A01N 43/78; C07C 93/06

[52] U.S. Cl. .................. 71/121; 71/88; 71/90; 71/92; 71/93; 71/94; 71/98; 71/100; 71/105; 71/111; 71/118; 544/113; 544/122; 544/129; 544/133; 544/141; 544/174; 544/194; 544/196; 544/197; 544/198; 544/199; 544/204; 544/205; 544/206; 544/207; 544/208; 544/209; 544/210; 544/211; 544/212; 544/213; 544/216; 544/217; 544/218; 544/219; 544/298; 544/299; 544/300; 544/301; 544/302; 544/303; 544/304; 544/306; 544/309; 544/310; 544/311; 544/312; 544/313; 544/315; 544/316; 544/317; 544/320; 544/322; 544/323; 544/324; 544/325; 544/326; 544/327; 544/328; 544/329; 544/330; 544/331; 544/335; 546/194; 546/281; 546/286; 546/287; 546/288; 546/289; 546/292; 546/294; 546/295; 546/296; 546/297; 546/298; 546/299; 546/301; 546/302; 546/303; 546/306; 546/307; 546/308; 546/309; 546/310; 546/311; 546/312; 546/315; 546/316; 546/322; 546/326; 546/330; 546/334; 548/183; 548/184; 548/185; 548/186; 548/191; 548/192; 548/193; 548/200; 548/201; 548/203; 549/61; 549/62; 549/63; 549/64; 549/65; 549/69; 549/72; 549/75; 549/474; 549/475; 549/476; 549/478; 549/479; 549/480; 549/481; 549/484; 549/485; 549/486; 549/487; 549/488; 549/495; 564/164; 564/347; 560/39; 560/138; 562/444; 260/455 R; 260/465 E; 71/95; 549/71

[58] Field of Search ............ 564/164, 285, 347, 341, 564/367, 370; 549/74, 75, 61, 62, 63, 64, 65, 69, 71, 72, 75, 474, 475, 476, 478, 479, 480, 481, 484, 485, 486, 487, 488, 495; 71/90, 121, 88, 92, 93, 94, 95, 100, 111, 118, 105, 98; 544/344, 113, 122, 129, 133, 141, 174, 194, 196, 197, 198, 199, 204, 205, 206, 207, 208, 209, 210, 211, 212, 213, 216, 217, 218, 219, 298, 299, 300, 301, 302, 303, 311, 312, 313, 315, 316, 317, 320, 322, 323, 324, 325, 326, 327, 328, 329, 330, 331, 335, 304, 306, 309, 310; 546/208, 194, 281, 286, 287, 288, 289, 292, 294, 295, 296, 297, 298, 299, 301, 302, 303, 306, 307, 308, 309, 310, 311, 312, 315, 316, 322, 326, 330, 334; 548/204, 183, 184, 185, 186, 191, 192, 193, 200, 201, 203

[56] References Cited

PUBLICATIONS

Wright, Brian J. et al., Chemical Abstracts, 93 (1980) #2102d and Formula Index p. 1863F.

Primary Examiner—Natalie Trousof
Assistant Examiner—L. Hendriksen
Attorney, Agent, or Firm—Frederick H. Rabin

[57] ABSTRACT

The novel compounds of the formula I are useful selective herbicides for postemergence application in crops of cereals, maize and rice.

In formula I,

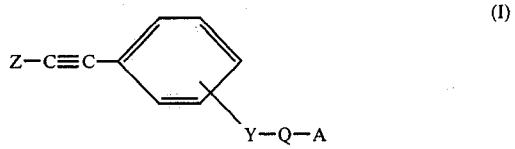

(I)

A is an unsubstituted or substituted amino group, Q is a $C_2$–$C_6$alkylene bridge, Y is an oxygen or sulfur atom or an unsubstituted or substituted nitrogen atom, and Z is an unsubstituted or substituted phenyl, naphthyl or heterocyclic radical, which phenyl radical, containing the bridge member Y, can additionally carry one to four further substituents.

19 Claims, No Drawings

HERBICIDAL HETEROCYCLIC AND SUBSTITUTED PHENYL PHENYLACETYLENE AMINES

The present invention relates to novel herbicidally active arylphenylacetylene compounds, to the production thereof, to compositions containing them, and to the use thereof for the selective control of weeds in different crops, e.g. cereals, maize and rice. The invention also relates to novel 1,1-dialkyl-3-arylpropargyl alcohols used as intermediates and to the production thereof.

The arylphenylacetylene compounds of this invention and the ammonium salts thereof, have the general formula I

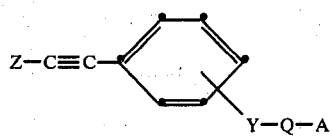  (I)

wherein

A is an unsubstituted or substituted amino group,
Q is a $C_2$–$C_6$alkylene bridge,
Y is an oxygen or a sulfur atom or an unsubstituted or substituted nitrogen atom, and
Z is an unsubstituted or substituted phenyl, naphthyl or heterocyclic radical, which phenyl radical carrying the substituent —Y—Q—A can additionally carry 1 to 4 further substituents, with the proviso that Z can only be an unsubstituted phenyl radical if the phenyl nucleus carrying the substituent —Y—Q—A carries a further substituent or the substituent —Y—Q—A is in the meta-position to the ethynyl bridge or —Y—Q—A is not —O—$CH_2$—$CH_2$—N($C_2H_5$)$_2$.

An unsubstituted or substituted amino group A is a primary, secondary or tertiary amino group. The alkylene bridge Q can be both straight-chain or branched. Heterocyclic ring systems Z are aromatic, non-condensed 5- to 6-membered rings containing oxygen, sulfur or nitrogen as ring member.

Preferred compounds are those of the formula Ia

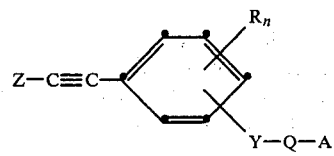  (Ia)

wherein

A is an amino group of the formula

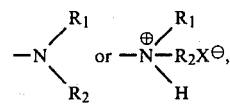

$R_1$ and $R_2$, each independently of the other, are hydrogen; $C_3$–$C_6$alkenyl, $C_3$–$C_6$alkynyl, $C_3$–$C_8$cycloalkyl; or $C_1$–$C_6$alkyl, unsubstituted or substituted by halogen, hydroxy, $C_1$–$C_4$alkoxy, alkoxycarbonyl containing at most 5 carbon atoms, cyano or carboxyl; or, together with the nitrogen atom to which they are attached, are also a 5- to 6-membered heterocyclic ring system containing altogether at most 2 hetero-atoms and which can be substituted by $C_1$–$C_3$alkyl, $X^\ominus$ is an anion,
Y is oxygen, sulfur or a radical —N—$R_4$—, in which $R_4$ is hydrogen, $C_3$–$C_6$alkenyl, $C_3$–$C_6$alkynyl, $C_3$–$C_8$cycloalkyl, or $C_1$–$C_6$alkyl which is unsubstituted or substituted by hydroxy, $C_1$–$C_4$alkoxy, alkoxycarbonyl containing at most 5 carbon atoms, cyano or carboxyl,
Q is a $C_2$–$C_6$alkylene bridge, unbranched or branched,
R is hydrogen, nitro, cyano, trifluoromethyl, $C_1$–$C_4$alkoxy, $C_1$–$C_4$alkylthio, —$NR_5R_6$, —CO—$NR_7R_8$, —$COOR_9$, —CO—$SR_{10}$, halogen, —$N_3$, or $C_1$–$C_4$alkyl which is unsubstituted or substituted by $C_1$–$C_4$alkyl, hydroxy, cyano or —$COOR_9$,
n is an integer from 1 to 4,
$R_5$, $R_7$, $R_8$, $R_9$ and $R_{10}$, each independently of the other, are hydrogen or $C_1$–$C_6$alkyl, $C_3$–$C_8$alkenyl or $C_3$–$C_8$alkynyl,
$R_6$ is hydrogen, $C_1$–$C_6$alkyl, $C_3$–$C_8$alkenyl, $C_3$–$C_8$alkynyl, —CO—$R_{11}$, —$COOR_{12}$ or —CO—$NHR_{13}$, in which $R_{11}$, $R_{12}$ and $R_{13}$ have the same meanings as $R_4$, and
Z is a phenyl, naphthyl or heterocyclic aromatic radical which contains at least one oxygen, sulfur or nitrogen atom, and which is unsubstituted or substituted by one or more radicals having the same meaning as R or which are formyl, —$SO_2$—$NR_7R_8$, —NH—$NH_2$, —NHOH, —SO—$R_9$, $SO_2$—$R_9$,

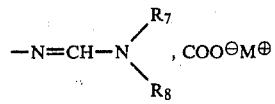

or $C_2$–$C_6$alkenyl which is unsubstituted or substituted by nitro, cyano or —$COOR_9$, and $M^\oplus$ is a sodium, potassium, calcium or magnesium cation, with the proviso that Z must be a substituted phenyl radical, or a naphthyl or heterocyclic radical, if —Y—Q—A is in the 4-position to Z—C≡C—, A is diethylamino, R is hydrogen, Q is ethylene and Y is oxygen.

Alkyl in the definitions of R and $R_1$ to $R_{13}$ is e.g. methyl, ethyl, n-propyl, isopropyl, the four isomers of butyl, as well as the straight-chain or branched pentyl, hexyl, heptyl or octyl radicals. However, alkyl is preferably straight- and short-chain and is, most preferably, ethyl or methyl.

Examples of alkoxy in the above definitions are methoxy, ethoxy, n-propyloxy, isopropyloxy or the four isomers of butyloxy, but is preferably methoxy or ethoxy.

Alkylthio is e.g. methylthio, ethylthio, n-propylthio or butylthio, with methylthio or ethylthio being preferred.

$C_3$–$C_8$Cycloalkyl is e.g. cyclopropyl, cyclobutyl, cyclopentyl, cyclohexyl, cycloheptyl or cyclooctyl, preferably cyclopropyl or, most preferably, cyclopentyl or cyclohexyl.

Examples of the anion $X^\ominus$ are the anions of organic and inorganic acids such as hydrohalic acids, phosphoric acid, sulfuric acid, aliphatic and aromatic sulfonic acids, fatty acids, as well as polyvalent oxyacids such as oxalic acid, malonic acid, succinic acid, adipic acid and citric acid. Preferably, however, the anions are halide ions such as chloride or bromide.

Examples of alkenyl radicals are allyl, and butenyl, pentenyl, hexenyl, heptenyl, octenyl, and the isomers thereof, Allyl is preferred.

Examples of alkynyl radicals are propargyl, and butynyl, pentynyl, hexynyl, octynyl, and the isomers thereof. Propargyl is preferred.

Aromatic heterocyclic ring systems are e.g. furyl, thienyl, triazolyl, pyridyl, oxazolyl, thiazolyl, thiadiazolyl, pyrrolyl, imidazolyl, pyrazolyl, pyrazinyl, pyrimidinyl, pyridazinyl, symmetrical and asymmetrical triazinyl or oxadiazolyl rings, with furyl, thienyl, pyridyl, pyrimidinyl, pyrrolyl, thiazolyl and triazinyl being preferred.

Preferred halogen substituents are chlorine, bromine and iodine.

Saturated heterocyclic ring systems are, as a rule, pyrrolidine, imidazolidine, pyrazolidine, piperidine, piperazine, piperimidine, morpholine and thiomorpholine.

The alkylene bridge Q is a straight-chain or branched structure, e.g. 1,2-ethylene; 1,3-propylene; 1,4-butylene; 1,5-pentylene; 1-methyl-1,2-ethylene; 2-methyl-1,2-ethylene; 1-ethyl-1,2-ethylene; 2-ethyl-1,2-ethylene; 1,2-dimethyl-1,2-ethylene; 1-methyl-1,3-propylene; 2-methyl-1,3-propylene; 3-methyl-1,3-propylene; 1-ethyl-1,3-propylene; 2-methyl-1,3-propylene. Preferably, however, the direct chain between the bridge atom Y and the nitrogen atom consists of 2 or 3 carbon atoms.

Preferred compounds of the formula Ia are those in which
(a) the radical —Y—Q—A is in the 4-position or
(b) in the 3-position to the arylethynyl radical,
(c) the direct alkylene bridge between the bridge atom Y and the nitrogen atom of the group A consists of 2 or 3 carbon atoms,
(d) the aryl radical Z is phenyl, furanyl or thienyl, each unsubstituted or substituted,
(e) pyridyl, pyrimidinyl, pyrrolyl, thiazolyl or triazinyl, each unsubstituted or substituted,
(f) the radicals $R_1$ and $R_2$ are methyl or ethyl, and
(g) the bridge member Y is oxygen.

Combination of the above features results in the further preferred groups of compounds of the formula Ia, in which
(aa) the radical —Y—Q—A is in the 4-position to the arylethynyl radical, the direct chain between the bridge atom Y and the nitrogen atom of the group A consists of 2 to 3 carbon atoms, the aryl radical Z is phenyl, furanyl or thienyl, each unsubstituted or substituted, the bridge member Y is oxygen, and $R_1$ and $R_2$ are methyl or ethyl,
(bb) the radical —Y—Q—A is in the 3-position to the arylethynyl radical, the direct chain between the bridge atom Y and the nitrogen atom of the group A consists of 2 or 3 carbon atoms, the aryl radical Z is phenyl, furanyl or thienyl, each unsubstituted or substituted, the bridge member Y is oxygen, and $R_1$ and $R_2$ are methyl or ethyl,
(cc) the radical —Y—Q—A is in the 4-position to the arylethynyl radical, the direct chain between the bridge atom Y and the nitrogen atom of the group A consists of 2 or 3 carbon atoms, the aryl radical Z is pyridyl, pyrimidinyl, pyrrolyl, thiazolyl or triazinyl, each unsubstituted or substituted, the bridge member Y is oxygen, and $R_1$ and $R_2$ are methyl or ethyl,
(dd) the radical —Y—Q—A is in the 3-position to the arylethynyl radical, the direct chain between the bridge atom Y and the nitrogen atom consists of 2 or 3 carbon atoms, the aryl radical Z is pyridyl, pyrimidinyl, pyrrolyl, thiazolyl or triazinyl, each unsubstituted or substituted, the bridge member Y is oxygen, and $R_1$ and $R_2$ are methyl or ethyl.

Particularly preferred compounds belonging to groups (aa), (bb), (cc) and (dd) of compounds of the formula Ia are those which, in addition to carrying the arylethynyl substituent and the group —Y—Q—A, carry at the central phenyl nucleus at most one further substituent selected from the group consisting of halogen, $C_1$–$C_4$alkyl, nitro or cyano.

Preferred individual compounds are:
1-[4-(4-methoxyphenylethynyl)phenoxy]-2-diethylaminoethane,
1-(3-phenylethynylphenoxy)-2-diethylaminoethane,
1-[4-(4-fluorophenylethynyl)phenoxy]-2-diethylaminoethane,
1-(4-phenylethynylphenoxy)-2-ethylmethylaminoethane,
1-[4-(2-thienylethynyl)phenoxy]-2-diethylaminoethane,
1-methyl-1-(3-phenylethynylphenoxy)-2-dimethylaminoethane and
2-methyl-1-(3-phenylethynylphenoxy)-2-dimethylaminoethane.

The arylphenylacetylene compounds of the formula I are novel and are obtained by the following methods, in which the formulae IV and X in reaction scheme A are to be understood as subformulae of I:

Scheme A:

Scheme A:

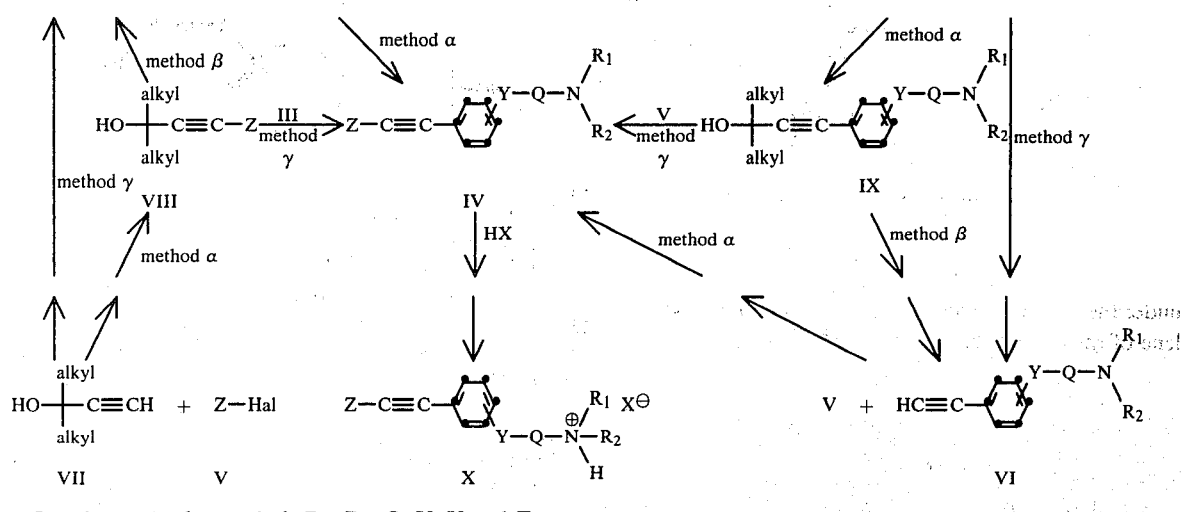

In scheme A, the symbols $R_1$, $R_2$, Q, X, Y and Z are as defined for formula I and Ia. Halogen is chlorine, but bromine and iodine are preferred.

Method α is a process which makes it possible, using metal catalysts, to bond halogenated aromatic radicals, as in formula III or V, to terminal acetylene groups, as in formulae II, VI and VII, under mild reaction conditions, in the presence of an acid acceptor. Reactions of this kind are described in the following publications: K. Sonogashira, Y. Tohda and N. Hagihara, Tetrahedron Lett., 50, 4467 (1975); L. Cassar, J. Organomet. Chem., 93, 253 (1975), and H. A. Dieck and F. R. Heck. J. Organomet. Chem., 93, 259 (1975).

This reaction advantageously takes place in organic solvents which are inert to the reactants. Suitable solvents of this kind are many protic and aprotic solvents, e.g. alkanols, ketones, ethers, hydrocarbons, halogenated hydrocarbons, aromatic solvents or also e.g. dimethyl formamide, dimethyl sulfoxide, acetonitrile or tertiary amines.

As dehydrohalogenation occurs during the reaction, a base can be used as acid acceptor. Suitable bases are e.g. strong inorganic bases such as triethylamine, diethylamine, pyridine, alcoholates etc. The amount of base employed in the reaction is from 1 to 5 equivalents.

As metal catalysts it is preferred to use palladium salts or complexes, in particular palladium chloride ($PdCl_2$), palladium acetate ($Pd(OCOCH_3)_2$), or the palladium dichlorobis(triphenylphosphine) complex $PdCl_2[P(C_6H_5)_3]_2$, usually with the addition of a copper(I) salt, especially of copper(I) iodide. The catalysts are employed by themselves or applied to a carrier, e.g. ground charcoal, alumina etc.

The reaction temperatures are generally in the range from 0° C. to 200° C., but are in the main between room temperature and the boiling point of the reaction mixture. As the reactions are often slightly exothermic, it is advantageous to raise the temperature in the reaction vessel for a short time in order to increase the reaction rate. The reaction times are generally from ½ hour to 48 hours.

Method β makes it possible, in the presence of a strong base such as NaOH, KOH or an alcoholate, to liberate the acetylene from a tertiary ethynyl ethanol, as in formulae VII, VIII and IX, which may be understood as a protected terminal acetylene group, with removal of the keto protective group, as in formulae II, VI and IX. The ketones obtained as by-products can be removed from the reaction mixture by distillation during the reaction. Reactions of this kind are described in German Offenlegungsschrift No. 2 905 507 and U.S. Pat. No. 4,128,588.

It is advantageous to conduct this reaction in inert organic solvents such as alcohols, ethers, ketones, hydrocarbons, halogenated hydrocarbons, aromatic solvents, or also in dimethyl formamide, dimethyl sulfoxide or acetonitrile. The reaction temperature in this case is also in the range between room temperature and the boiling point of the solvent. The reaction time is generally from ½ hour to 12 hours.

Method γ is a combination of methods α and β, except that the acetylene to be reacted by method α is prepared in situ by treating a protected acetylene of the formula VII, VIII and IX with a strong base. The reaction conditions are identical with those of method α. However, the addition of a strong base such as NaOH, KOH or the alkali metal salt of an alcohol, is mandatory.

In the process of this invention, compounds of the formula IV

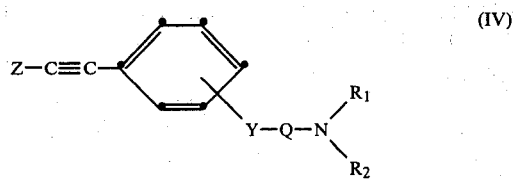

are obtained either by reacting an ethynyl compound of the formula II $$Z-C\equiv CH \qquad (II)$$

in the presence of an acid acceptor and of a metal catalyst, optionally in an inert gas atmosphere, with a phenyl halide of the formula III

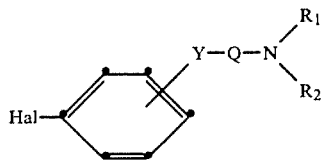 (III)

or by reacting an aromatic halide of the formula V

Z—Hal      (V)

under the same reaction conditions, with a phenylacetylene of the formula VI

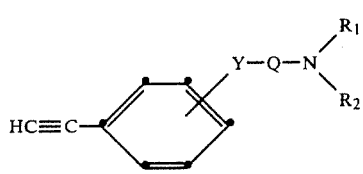 (VI)

in which formulae above $R_1$, $R_2$, Y, Q and Z are as defined for formula Ia and Hal is bromine or iodine.

In a further process of the invention, the compounds of the formula IV are obtained by reacting an aromatic halide of the formula V Z—Hal      (V)

in the presence of an acid acceptor and of a metal catalyst, optionally in an inert gas atmosphere, with a propargyl alcohol of the formula VII

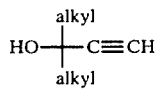 (VII)

and reacting the resultant ethynyl compound of the formula VIII

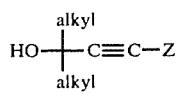 (VIII)

in the presence of a strong base and of a metal catalyst, optionally in an inert gas atmosphere, with a phenyl halide of the formula III

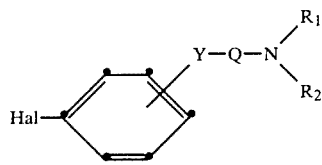 (III)

or a reacting the phenyl halide of the formula III, under the above reaction conditions, initially with the propargyl alcohol of the formula VII and then reacting the resultant ethynyl compound of the formula IX

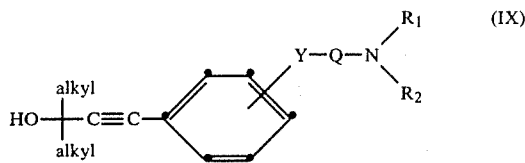 (IX)

under the above reaction conditions, with the aromatic halide of the formula V, in which formulae above $R_1$, $R_2$, Q, Y and Z are as defined for formula IV, Hal is bromine or iodine, and alkyl is a $C_1$–$C_4$alkyl radical.

The 1,1-dialkyl-3-arylpropargyl alcohols of the formulae VIII and IX, which are also novel and which have been specially developed as intermediates for obtaining the compounds of the formula I, are prepared in a manner similar to that of the first reaction step of the above described process, by reacting halides of the formula V or VI with a propargyl alcohol of the formula VII. The compounds of the formulae VIII and IX likewise constitute an object of the invention.

In a further process, the compounds of the formula X

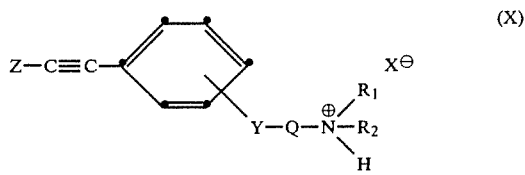 (X)

are obtained by reacting the compounds of the formula IV with an acid HX, in which formulae $R_1$, $R_2$, Q, X, Y and Z are as defined for formulae I and Ia.

The starting materials of the formulae II, III, V, VI and VII are known or readily obtainable and/or commercially available.

The novel compounds of the formula I are stable compounds. The compounds of the subformula IV have relatively good solubility in conventional organic solvents and are poorly soluble in water. They can be readily precipitated from the reaction solution by the addition of water. They are formulated to liquid herbicidal compositions with the aid of conventional solubilisers and/or dispersants.

The compounds of the subformula X are readily soluble in water, but are relatively poorly soluble even in polar organic solvents such as dimethyl sulfoxide, dimethyl formamide or acetonitrile.

The herbicidal activity of 1-(4-phenylethynylphenoxy)-2-diethylaminoethane has been recently discovered and was disclosed for the first time in Phytochemistry, 19, 61 (1980).

The arylphenylacetylene compounds of the formula I influence plant growth and, in postemergence application, have an excellent selective herbicidal action against resistant broad-leafed weeds such as Galium, Veronica, Viola, and also against Sinapis, Chrysanthemum etc., in maize and rice crops, but primarily in crops of cereals. Perennial weeds in particular are effectively controlled by the translocation of the compounds of formula I. By translocation is meant the transportion of an active ingredient within the plant. The active ingredient can be translocated from the leaves to the roots and vice versa, and there exert its action.

The compounds of the formula I are translocatable, i.e. weeds are damaged right through to the roots by them, e.g. by leaf application.

The compounds of the formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. The methods of application, such as spraying, atomising, dusting, scattering or pouring, are chosen in accordance with the intended objectives and the prevailing circumstances, just like the nature of the compositions.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable solids such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of preganulated materials of inorganic or organic nature can be used, e.g. especially dolomite or pulverised plant residues.

Depending on the nature of the active ingredient to be formulated, suitable surface-active compounds are nonionic, cationic and/or anionic surfactants having good emulsifying, dispersing and wetting properties. The term "surfactants" will also be understood as comprising surfactant mixtures.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methaltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of adducts of fatty alcohols and ethylene oxide. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminepolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenol-polyethoxyethanols, castor oil polyglycol ethers, polypropylene/polyethylene oxide, adducts, tributylphenoxypolyethoxyethanol, polyethylene glycol and octylphenoxypolyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one polyglycol ether or $C_8$–$C_{22}$alkyl radical and, as further substituents, lower unsubstituted or halogenated alkyl, benzyl or lower hydroxylalkyl radicals or fatty acid. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications: "McCutcheon's Detergents and Emulsifiers Annual," MC Publishing Corp., Ringwood, New Jersey, 1979; Sisely and Wood, "Encyclopedia of Surface Active Agents," Chemical Publishing Co. Inc., New York, 1964.

The pesticidal formulations usually contain 0.1 to 99%, preferably 0.1 to 95%, of a compound of the formula I, 1 to 99.9% of a solid or liquid adjuvant, and 0 to 25%, preferably 0.1 to 25%, of a surfactant.

Preferred formulations are composed in particular of the following constituents (%=percentage by weight):
Solutions
    active ingredient: 5 to 95%, preferably 10 to 80%
    solvent: 95 to 5%, preferably 90 to 0%
    surfactant: 1 to 30%, preferably 2 to 20%

Emulsifiable concentrates
   active ingredient: 10 to 50%, preferably 10 to 40%
   surfactant: 5 to 30%, preferably 10 to 20%
   liquid carrier: 20 to 95%, preferably 40 to 80%
Dusts
   active ingredient: 0.5 to 10%, preferably 2 to 8%
   solid carrier: 99.5 to 90%, preferably 98 to 2%
Suspension concentrates
   active ingredient: 5 to 75%, preferably 10 to 50%
   water: 94 to 25%, preferably 90 to 30%
   surfactant: 1 to 40%, preferably 2 to 30%
Wettable powders
   active ingredient: 5 to 90%, preferably 10 to 80% and, most preferably, 20 to 60%
   surfactant: 0.5 to 20%, preferably 1 to 15%
   solid carrier: 5 to 90%, preferably 30 to 70%
Granulates
   active ingredient: 0.5 to 30%, preferably 3 to 15%
   solid carrier: 99.5 to 70%, preferably 97 to 85%.

Whereas commercial products will be preferably formulated as concentrates, the end user will normally employ dilute formulations. The formulations can be diluted to a concentration as low as 0.001%. The rates of application are normally 0.1 to 10 kg a.i./ha, preferably 0.25 to 5 kg a.i./ha.

The formulations can also contain further additives such as stabilisers, antifoams, viscosity regulators, binders, adhesives, as well as fertilisers or other active compounds, in order to attain special effects.

The invention is further illustrated by the following Examples. Pressures are given in millibars (mb).

PREPARATORY EXAMPLES

EXAMPLE 1

1-(3-phenylethynylphenoxy)-2-diethylaminoethane (Compound 1)

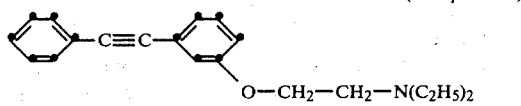

O—CH$_2$—CH$_2$—N(C$_2$H$_5$)$_2$

To a solution of 15 g (0.06 mole) of 1-(3-bromophenoxy)-2-diethylaminoethane and 6.12 g (0.06 mole) of phenylacetylene in 150 ml of triethylamine are added, under nitrogen, 420 mg of the palladium complex PdCl$_2$[P(C$_6$H$_5$)$_3$]$_2$ and 228 mg of copper (I) iodide. This reaction mixture is refluxed for 24 hours, then concentrated, and the residue is taken up in water. After extraction with 200 ml of ether, the combined ethereal phases are washed 4 times with water, dried, and evaporated to dryness. The crude product is chromatographed on silica gel and then distilled, affording 13.1 g (75%) of 1-(3-phenylethynylphenoxy)-2-diethylaminoethane with a boiling point of 150°–160° C./0.02 mb and a refractive index of n$_D^{25}$:1.5858.

EXAMPLE 2

1-(2,5-dichloro-4-phenylethynylphenoxy)-2-diethylaminoethane (Compound 407)

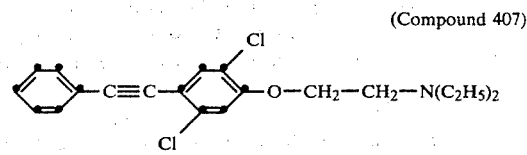

To a solution of 19.4 g (0.05 mole) of 1-(2,5-dichloro-4-iodophenoxy)-2-diethylaminoethane and 5.2 g (0.053 mole) of phenylacetylene in 250 ml of triethylamine are added, under nitrogen, 200 mg of the palladium complex PdCl$_2$[P(C$_6$H$_5$)$_3$]$_2$ and 100 mg of copper(I) iodide. After the weakly exothermic reaction has subsided, the reaction mixture is stirred for 15 hours at room temperature, then concentrated, and the residue is taken up in water. After extraction with 200 ml of ether, the combined ethereal phases are washed 4 times with water, dried and evaporated to dryness. The crude product is chromatographed on silica gel, affording 14.3 g (79%) of 1-(2,5-dichloro-4-phenylethynylphenoxy)-2-diethylaminoethane with a refractive index of n$_D^{25}$:1.6173.

EXAMPLE 3

1-[4-(4-methoxyphenylethynyl)phenoxy]-2-diethylaminoethane (Compound 433)

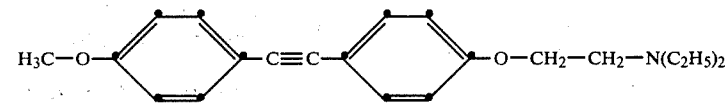

To a solution of 15 g (0.06 mole) of 1-(4-bromophenoxy)-2-diethylaminoethane and 8.2 g (0.062 mole) of 4-methoxyphenylacetylene in 150 ml of triethylamine are added, under nitrogen, 420 mg of the palladium complex PdCl$_2$[P(C$_6$H$_5$)$_2$]$_2$ and 228 mg of copper(I) iodide. The reaction mixture is subsequently refluxed for 24 hours, then concentrated, and the residue is taken up in water. After extraction with 200 ml of ether, the combined ethereal phases are washed 3 times with water, dried and evaporated to dryness. The crude product is chromatographed on silica gel, affording 15.5 g (80%) of 1-[4-(4-methoxyphenylethynyl)phenoxy]-2-diethylaminoethane with a melting point of 59°–60° C.

EXAMPLE 4

1-[4-(2-thienylethynyl)phenoxy]-2-diethylaminoethane (Compound 471)

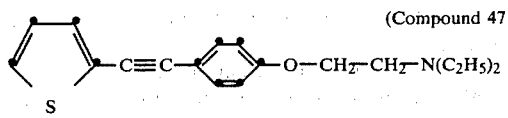

(a) To 142 g (0.45 mole) of 1-(4'-iodophenoxy)-2-diethylaminoethane, 1.2 liters of triethylamine and 37.8 g (0.45 mole) of 3-methyl-1-butin-3-ol are added, under nitrogen, 3.4 g of the palladium complex PdCl$_2$[P(C$_6$H$_5$)$_3$]$_2$ and 1.9 g of copper(I) iodide. After the exothermic reaction has subsided, the reaction mixture is stirred for 15 hours at room temperature, then filtered, and the solution is evaporated in vacuo to dryness. The oily residue crystallises immediately. The product is dried in vacuo at 40° C., affording 123 g (99%) of 1-(3-hydroxy-3-methyl-1-butyn-1-yl)-4-(2-diethylaminoethoxy)benzene with a melting point of 64° C.

(b) To a solution of 11.07 g (0.04 mole) of 1-(3-hydroxy-3-methyl-1-butyn-1-yl)-4-(2-diethylaminoethoxy)benzene and 8.4 g (0.04 mole) of 2-iodothiophene in 135 ml of triethylamine are added, under nitrogen, 4.95 g of pulverised potassium hydroxide. Then 310 mg of the palladium complex PdCl$_2$[P(C$_6$H$_5$)$_3$]$_2$ and 180 ml of copper(I) iodide are added and the reaction mixture is stirred for 20 hours at boiling temperature. The reaction mixture is taken up in 250 ml of ether and the solution is washed 3 times with 100 ml of water and once with saturated sodium chloride solution, dried over sodium sulfate and evaporated to dryness. The residue is chromatographed on silica gel with 96% of ether/4% of methanol (saturated with NH$_3$), affording 9 g (75%) of 1-[4-(2-thienylethynyl)phenoxy]-2-diethylaminoethane in the form of a colourless oil with a refractive index of $n_D^{30}$:1.6170.

EXAMPLE 5

1-[4-(4-fluorophenylethynyl)phenoxy]-2-diethylaminoethane (Compound 416)

(a) To a solution of 35.2 g (0.19 mole) of 4-bromofluorobenzene and 25.2 g (0.3 mole) of 3-hydroxy-3-methyl-1-butine in 250 ml of triethylamine are added, under nitrogen, 1 g of the palladium complex PdCl$_2$[P(C$_6$H$_5$)$_3$]$_2$ and 0.2 g of copper(I) iodide. The reaction mixture is subsequently stirred for 24 hours at 70° C. After filtering off triethylammonium bromide and removing excess triethylamine by evaporation, the residue is taken up in 200 ml of ether and the solution is washed twice with 100 ml of 5% aqueous HCl solution and 100 ml of water, dried, treated with activated charcoal, and evaporated to dryness. The residue is chromatographed on silica gel with a 1:1 mixture of ether/hexane, affording 26.4 g (78%) of 1-fluoro-4-(3-hydroxy-3-methyl-1-butyn-1-yl)-benzene with a melting point of 124° C.

(b) To a solution of 25.2 g (0.1 mole) of 1-4-(bromophenoxy)-2-diethylaminoethane and 17.8 g (0.1 mole) of 1-fluoro-4-(3-hydroxy-3-methyl-1-butyn-1-yl)benzene in 250 ml of triethylamine are added, under nitrogen, 11.2 g of pulverised potassium hydroxide, 0.7 g of the palladium complex PdCl$_2$[P(C$_6$H$_5$)$_3$]$_2$ and 0.13 g of copper(I) iodide. The reaction mixture is subsequently stirred for 14 hours at 80° C. The reaction mixture is taken up in 250 ml of ether and the solution is washed twice with 100 ml of water and 100 ml of aqueous K$_2$CO$_3$ solution, treated with activated charcoal and evaporated to dryness. Vacuum distillation of the residue yields 9.5 g (33%) of 1-[4-(4-fluorophenylethynyl)-phenoxy]-2-diethylaminoethane with a boiling point of 156°–162° C./0.08 mb.

The compounds obtained in the foregoing Examples and others prepared in analogous manner are listed in the following table:

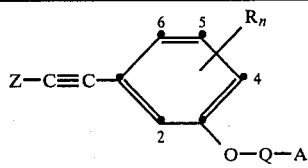

| No. | Z | $R_n$ | Q | A | Physical data (°C.) |
|---|---|---|---|---|---|
| 1 | C$_6$H$_5$— | H | —(CH$_2$)$_2$— | —N(C$_2$H$_5$)$_2$ | b.p: 150–160°/ 0.02mb $n_D^{25}$: 1.5858 |
| 2 | C$_6$H$_5$— | H | —(CH$_2$)$_2$— | —N⟨pyrrolidine⟩ | |
| 3 | C$_6$H$_5$— | H | —(CH$_2$)$_2$— | —N⟨morpholine⟩ | |
| 4 | C$_6$H$_5$— | H | —(CH$_2$)$_3$— | —N(C$_2$H$_5$)$_2$ | |
| 5 | C$_6$H$_5$— | H | —(CH$_2$)$_2$— | —NHC$_2$H$_5$ | |
| 6 | C$_6$H$_5$— | H | —(CH$_2$)$_2$— | —N(C$_2$H$_5$)$_2$.HCl | |
| 7 | C$_6$H$_5$— | 4-Cl | —(CH$_2$)$_2$— | —N(C$_2$H$_5$)$_2$ | |
| 8 | C$_6$H$_5$— | 4-NO$_2$ | —(CH$_2$)$_2$— | —N(C$_2$H$_5$)$_2$ | |
| 9 | C$_6$H$_5$— | 4-CN | —(CH$_2$)$_2$— | —N(C$_2$H$_5$)$_2$ | |
| 10 | C$_6$H$_5$— | 4-CH$_3$ | —(CH$_2$)$_2$— | —N(C$_2$H$_5$)$_2$ | |
| 11 | C$_6$H$_5$— | 4-C$_2$H$_5$ | —(CH$_2$)$_2$— | —N(C$_2$H$_5$)$_2$ | |
| 12 | C$_6$H$_5$— | 4-OCH$_3$ | —(CH$_2$)$_2$— | —N(C$_2$H$_5$)$_2$ | |
| 13 | C$_6$H$_5$— | 4-CH$_3$, 6-CH$_3$ | —(CH$_2$)$_2$— | —N(C$_2$H$_5$)$_2$ | |
| 14 | C$_6$H$_5$— | 4-Cl, 6-CH$_3$ | —(CH$_2$)$_2$— | —N(C$_2$H$_5$)$_2$ | |
| 15 | C$_6$H$_5$— | 2-CH$_3$, | —(CH$_2$)$_2$— | —N(C$_2$H$_5$)$_2$ | |

-continued

| | | | | | |
|---|---|---|---|---|---|
| 16 | C₆H₅— | 4-CH₃, 2-CH₃, 6-CH₃ | —(CH₂)₂— | —N(C₂H₅)₂ | |
| 17 | C₆H₅— | 4-Cl | —(CH₂)₃— | —N(C₂H₅)₂ | |
| 18 | C₆H₅— | 4-Cl | —(CH₂)₃— | 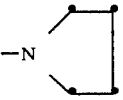 | |
| 19 | C₆H₅— | 4-NO₂ | —(CH₂)₃— | —N(C₂H₅)₂ | |
| 20 | C₆H₅— | 4-CH₃ | —(CH₂)₃— | —N(C₂H₅)₂ | |
| 21 | C₆H₅— | 4-Cl | —(CH₂)₃— | —N(CH₃)₂ | |
| 22 | C₆H₅— | 4-OCH₃ | —(CH₂)₃— | —N(CH₃)₂ | |
| 23 | 4-Cl—C₆H₄— | H | —(CH₂)₂— | —N(C₂H₅)₂ | |
| 24 | 4-Cl—C₆H₄— | 4-Cl | —(CH₂)₂— | —N(C₂H₅)₂ | |
| 25 | 4-CF₃—C₆H₄— | H | —(CH₂)₂— | —N(C₂H₅)₂ | |
| 26 | 4-CF₃—C₆H₄— | H | —(CH₂)₃— | —N(C₂H₅)₂ | |
| 27 | 4-CF₃—C₆H₄— | 4-NO₂ | —(CH₂)₂— | —N(C₂H₅)₂ | |
| 28 | 4-CF₃-2-Cl—C₆H₃— | H | —(CH₂)₂— | —N(C₂H₅)₂ | |
| 29 | 4-CF₃-2-Cl—C₆H₃— | 4-OCH₃ | —(CH₂)₂— | —N(C₂H₅)₂ | |
| 30 | 4-CF₃-2-Cl—C₆H₃— | H | —(CH₂)₃— | —N(C₂H₅)₂ | |
| 31 | 3-CH₃-5-CH₃—C₆H₃— | H | —(CH₂)₂— | —N(C₂H₅)₂ | |
| 32 | 3-CH₃-5-CH₃—C₆H₃— | 4-Cl | —(CH₂)₂— | —N(C₂H₅)₂ | |
| 33 | 3-CH₃-5-CH₃—C₆H₃— | H | —(CH₂)₃— | —N(C₂H₅)₂ | |
| 34 | 4-iC₃H₇—C₆H₄— | H | —(CH₂)₃— | —N(C₂H₅)₂ | |
| 35 | 4-iC₃H₇—C₆H₄— | H | —(CH₂)₂— | —N(C₂H₅)₂ | |
| 36 | 4-CN—C₆H₄— | H | —(CH₂)₂— | —N(C₂H₅)₂ | |
| 37 | 4-CN—C₆H₄— | 4-CH₃ | —(CH₂)₂— | —N(C₂H₅)₂ | |
| 38 | 4-NO₂—C₆H₄— | H | —(CH₂)₂— | —N(C₂H₅)₂ | |
| 39 | 4-NO₂—C₆H₄— | H | —(CH₂)₃— | —N(C₂H₅)₂ | |
| 40 | 4-NO₂—C₆H₄— | 4-C₂H₅ | —(CH₂)₂— | —N(C₂H₅)₂ | |
| 41 | 2-NO₂-4-Cl—C₆H₃— | H | —(CH₂)₂— | —N(C₂H₅)₂ | |
| 42 | 2-NO₂-4-Cl—C₆H₃— | 4-Cl | —(CH₂)₂— | —N(C₂H₅)₂ | |
| 43 | 2-C₂H₅-6-CH₃—C₆H₃— | H | —(CH₂)₂— | —N(C₂H₅)₂ | |
| 44 | 2-C₂H₅-6-CH₃—C₆H₃— | H | —(CH₂)₂— | —N(OCH₃)CH₃ | |
| 45 | 2-C₂H₅-6-CH₃—C₆H₃— | 4-NO₂ | —(CH₂)₂— | —N(C₂H₅)₂ | |
| 46 | 4-OCH₃—C₆H₄— | H | —(CH₂)₂— | —N(C₂H₅)₂ | $n_D^{25}$: 1.6092 |
| 47 | 4-OCH₃—C₆H₄— | 4-Cl | —(CH₂)₂— | —N(C₂H₅)₂ | |
| 48 | 4-SC₂H₅—C₆H₄— | H | —(CH₂)₂— | —N(C₂H₅)₂ | |
| 49 | 4-F—C₆H₄— | H | —(CH₂)₂— | —N(C₂H₅)₂ | $n_D^{25}$: 1.5818 |
| 50 | 3-CF₃—C₆H₄— | H | —(CH₂)₂— | —N(C₂H₅)₂ | |
| 51 | 3-CF₃—C₆H₄— | H | —(CH₂)₃— | —N(C₂H₅)₂ | |
| 52 | 3-CF₃—C₆H₄— | H | —(CH₂)₃— | —N(CH₃)₂ | |
| 53 | 3-CF₃-5-CF₃—C₆H₃— | H | —(CH₂)₂— | —N(C₂H₅)₂ | |
| 54 | 3-CF₃-5-CF₃—C₆H₃— | H | —(CH₂)₂— | —N(OCH₃)CH₃ | |
| 55 | 3-CF₃-5-CF₃—C₆H₃— | 4-CH₃ | —(CH₂)₂— | —N(OCH₃)CH₃ | |
| 56 | 3-CN—C₆H₄— | H | —(CH₂)₂— | —N(C₂H₅)₂ | |
| 57 | 3-CN—C₆H₄— | H | —(CH₂)₃— | —N(C₂H₅)₂ | |
| 58 | 3-CN—C₆H₄— | 4-Cl | —(CH₂)₂— | —N(C₂H₅)₂ | |
| 59 | 3-CN—C₆H₄— | H | —(CH₂)₃— | —N(CH₃)₂ | |
| 60 | 3-COOCH₃—C₆H₄— | H | —(CH₂)₂— | —N(C₂H₅)₂ | |
| 61 | 3-COOCH₃—C₆H₄— | H | —(CH₂)₃— | —N(CH₃)₂ | |
| 62 | 3-COOCH₃—C₆H₄— | H | —(CH₂)₃— | —N(OCH₃)CH₃ | |
| 63 | 3-COOCH₃—C₆H₄— | 4-NO₂ | —(CH₂)₂— | —N(C₂H₅)₂ | |
| 64 | 3-OCH₃—C₆H₄— | H | —(CH₂)₂— | —N(C₂H₅)₂ | |
| 65 | 3-OCH₃—C₆H₄— | H | —(CH₂)₃— | —N(C₂H₅)₂ | |
| 66 | 3-OCH₃—C₆H₄— | 4-CN | —(CH₂)₃— | —N(C₂H₅)₂ | |
| 67 | 3-OCH₃—C₆H₄— | 4-CN | —(CH₂)₂— | —N(C₂H₅)₂ | |
| 68 | 3-CON(CH₃)₂—C₆H₄— | H | —(CH₂)₂— | —N(C₂H₅)₂ | |
| 69 | 3-CON(CH₃)₂—C₆H₄— | H | —(CH₂)₃— | —N(C₂H₅)₂ | |
| 70 | 3-CON(CH₃)₂—C₆H₄— | 4-Cl | —(CH₂)₂— | —N(C₂H₅)₂ | |
| 71 | 3-CON(CH₃)₂—C₆H₄— | H | —(CH₂)₂— | —N(nC₄H₉)₂ | |
| 72 | 3-COSC₂H₅—C₆H₄— | H | —(CH₂)₂— | —N(C₂H₅)₂ | |
| 73 | 3-COSC₂H₅—C₆H₄— | H | —(CH₂)₃— | —N(C₂H₅)₂ | |
| 74 | 3-COSC₂H₅—C₆H₄— | 4-NO₂ | —(CH₂)₂— | —N(C₂H₅)₂ | |
| 75 | 3-COSC₂H₅—C₆H₄— | 4-NO₂ | —(CH₂)₂— | —N(nC₄H₉)₂ | |
| 76 | Cl-pyrimidinyl | H | —(CH₂)₂— | —N(C₂H₅)₂ | |
| 77 | Cl-pyrimidinyl | H | —(CH₂)₃— | —N(C₂H₅)₂ | |

-continued

| # | Structure | R | Linker | Amine |
|---|---|---|---|---|
| 78 | 3,4-diCl-pyridyl | H | —(CH₂)₂— | —N(C₂H₅)₂ |
| 79 | 3,4-diCl-pyridyl | 4-NO₂ | —(CH₂)₂— | —N(C₂H₅)₂ |
| 80 | 3,4-diCl-pyridyl | 4-Cl | —(CH₂)₃— | —N(CH₃)₂ |
| 81 | 3-CF₃-pyridyl | H | —(CH₂)₂— | —N(C₂H₅)₂ |
| 82 | 3-CF₃-pyridyl | 4-NO₂ | —(CH₂)₂— | —N(C₂H₅)₂ |
| 83 | 3-CF₃-4-Cl-pyridyl | H | —(CH₂)₂— | —N(C₂H₅)₂ |
| 84 | 3-CF₃-4-Cl-pyridyl | H | —(CH₂)₃— | —N(C₂H₅)₂ |
| 85 | 3-I-pyridyl | H | —(CH₂)₂— | —N(C₂H₅)₂ |
| 86 | 3-I-pyridyl | H | —(CH₂)₃— | —N(C₂H₅)₂ |
| 87 | 3-Cl-4-CN-pyridyl | H | —(CH₂)₂— | —N(C₂H₅)₂ |
| 88 | 3-Cl-4-CN-pyridyl | 4-CH₃ | —(CH₂)₂— | —N(C₂H₅)₂ |
| 89 | 3-CN-pyridyl | H | —(CH₂)₂— | —N(C₂H₅)₂ |

-continued
| | | | | |
|---|---|---|---|---|
| 90 | 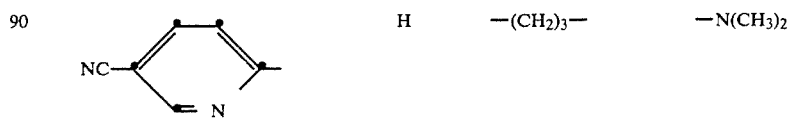 | H | $-(CH_2)_3-$ | $-N(CH_3)_2$ |
| 91 | 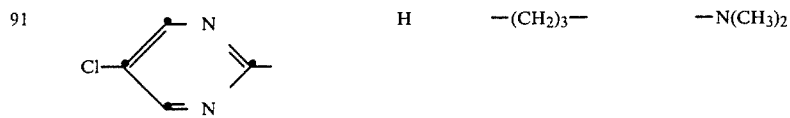 | H | $-(CH_2)_3-$ | $-N(CH_3)_2$ |
| 92 | 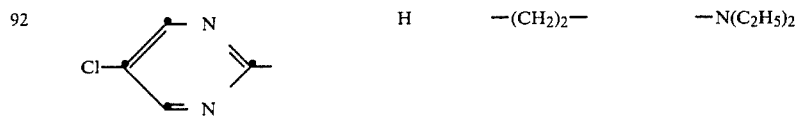 | H | $-(CH_2)_2-$ | $-N(C_2H_5)_2$ |
| 93 | 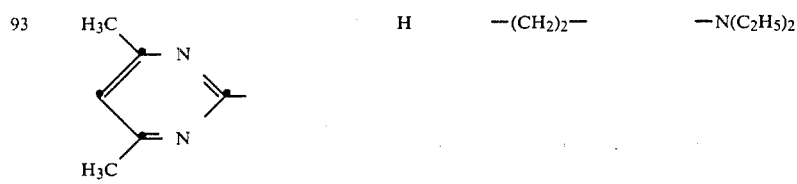 | H | $-(CH_2)_2-$ | $-N(C_2H_5)_2$ |
| 94 | 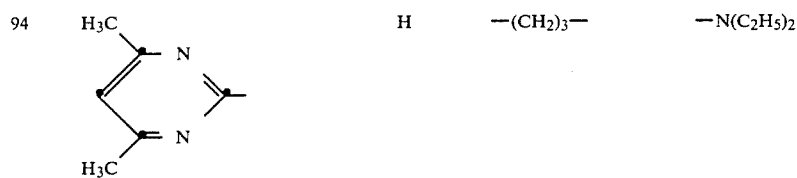 | H | $-(CH_2)_3-$ | $-N(C_2H_5)_2$ |
| 95 | 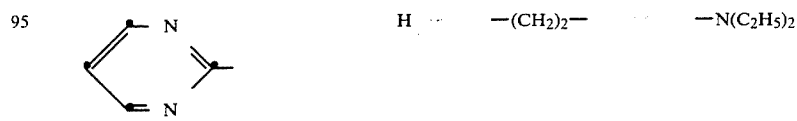 | H | $-(CH_2)_2-$ | $-N(C_2H_5)_2$ |
| 96 | 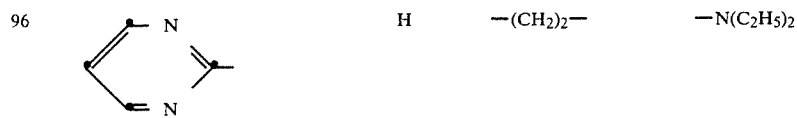 | H | $-(CH_2)_2-$ | $-N(C_2H_5)_2$ |
| 97 | 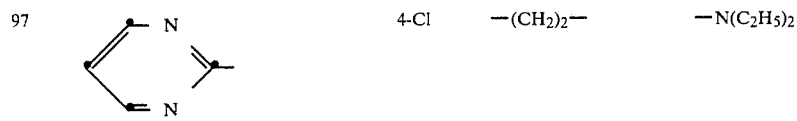 | 4-Cl | $-(CH_2)_2-$ | $-N(C_2H_5)_2$ |
| 98 | 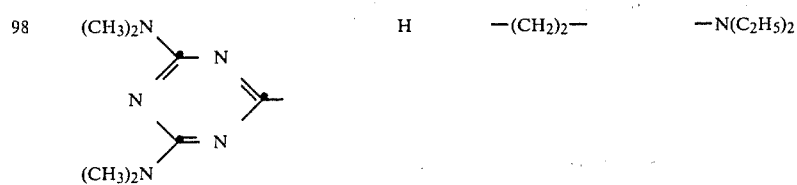 | H | $-(CH_2)_2-$ | $-N(C_2H_5)_2$ |
| 99 | 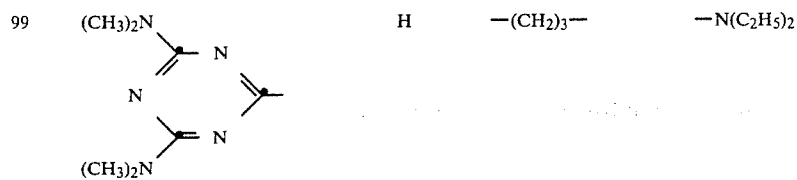 | H | $-(CH_2)_3-$ | $-N(C_2H_5)_2$ |

| | | | | |
|---|---|---|---|---|
| 100 | triazine with H3CO, (CH3)2N substituents | H | —(CH2)3— | —N(C2H5)2 |
| 101 | triazine with H3CO, (CH3)2N substituents | H | —(CH2)2— | —N(C2H5)2 |
| 102 | triazine with H3CO, (CH3)2N substituents | 4-NO2 | —(CH2)2— | —N(C2H5)2 |
| 103 | triazine with H3CO, H3CO substituents | H | —(CH2)2— | —N(C2H5)2 |
| 104 | triazine with H3CO, H3CO substituents | H | —(CH2)3— | —N(C2H5)2 |
| 105 | thiophene | H | —(CH2)3— | —N(C2H5)2 |
| 106 | thiophene | H | —(CH2)2— | —N(C2H5)2 |
| 107 | 2-methylthiophene | H | —(CH2)2— | —N(C2H5)2 |
| 108 | 2-methylthiophene | 4-Cl | —(CH2)2— | —N(C2H5)2 |
| 109 | furan | H | —(CH2)2 | —N(C2H5)2 |
| 110 | furan | H | —(CH2)3— | —N(C2H5)2 |

-continued

| # | Ar | R | Alkylene | Amine |
|---|---|---|---|---|
| 111 | 3-(F₃C)-1,2,4-thiadiazol-5-yl | H | —(CH₂)₃— | —N(C₂H₅)₂ |
| 112 | 3-(F₃C)-1,2,4-thiadiazol-5-yl | H | —(CH₂)₂— | —N(C₂H₅)₂ |
| 113 | imidazol-2-yl | H | —(CH₂)₃— | —N(C₂H₅)₂ |
| 114 | thiazol-2-yl | H | —(CH₂)₃— | —N(C₂H₅)₂ |
| 115 | oxazol-2-yl | H | —(CH₂)₃— | —N(C₂H₅)₂ |
| 116 | oxazol-2-yl | H | —(CH₂)₂— | —N(C₂H₅)₂ |
| 117 | α-Naphthyl | H | —(CH₂)₂— | —N(C₂H₅)₂ |
| 118 | α-Naphthyl | H | —(CH₂)₃— | —N(C₂H₅)₂ |
| 119 | α-Naphthyl | 4-Cl | —(CH₂)₂— | —N(C₂H₅)₂ |
| 120 | α-Naphthyl | 4-NO₂ | —(CH₂)₂— | —N(C₂H₅)₂ |
| 121 | α-Naphthyl | 4-OCH₃ | —(CH₃)₂— | —N(C₂H₅)₂ |
| 122 | β-Naphthyl | H | —(CH₂)₂— | —N(C₂H₅)₂ |
| 123 | β-Naphthyl | H | —(CH₂)₃— | —N(C₂H₅)₂ |
| 124 | β-Naphthyl | 4-Cl | —(CH₂)₂— | —N(C₂H₅)₂ |
| 125 | β-Naphthyl | 4-NO₂ | —(CH₂)₂— | —N(C₂H₅)₂ |
| 126 | β-Naphthyl | 4-CN | —(CH₂)₂— | —N(C₂H₅)₂ |
| 127 | pyridyl | H | —(CH₂)₂— | —N(C₂H₅)₂ |
| 128 | C₆H₅— | H | —(CH₂)₂— | —N(C₂H₅)—CH₂—COOC₂H₅ |
| 129 | C₆H₅— | H | —(CH₂)₂— | —N(C₂H₅)—CH₂—COOH |
| 130 | C₆H₅— | H | —(CH₂)₂— | —N(CH₂—CH₂OH)₂ |
| 131 | C₆H₅— | H | —(CH₂)₂— | —N(C₂H₅)—CH₂—CH₂—O—CH₃ |
| 132 | C₆H₅— | H | —CH(CH₃)—CH₂— | —N(CH₃)₂ |
| 133 | C₆H₅— | H | —CH(CH₃)—CH₂— | —N(C₂H₅)₂ |
| 134 | C₆H₅— | H | —CH₂—CH(CH₃)— | —N(CH₃)₂ |
| 135 | C₆H₅— | H | —CH₂—CH(CH₃)— | —N(CH₃)(C₂H₅) |
| 136 | C₆H₅— | H | —CH(CH₃)—CH(CH₃)— | —N(CH₃)(C₂H₅) |

-continued

| | | | | |
|---|---|---|---|---|
| 137 | $C_6H_5-$ | 4-CN | $-CH_2-CH(C_2H_5)-$ | $-N(CH_3)_2$ |
| 138 | $C_6H_5-$ | 4-Cl | $-(CH_2)_2-CH(CH_3)-$ | $-N(CH_3)-C_3H_7(n)$ |
| 139 | $4-F-C_6H_4-$ | H | $-CH(CH_3)-CH_2-$ | $-N(CH_3)_2$ |
| 140 | $4-F-C_6H_4-$ | H | $-CH(CH_3)-(CH_2)_2-$ | $-N(C_2H_5)_2$ |
| 141 | $4-F-C_6H_4-$ | H | $-CH_2-CH(CH_3)-CH_2-$ | $-N(C_2H_5)_2$ |
| 142 | $4-F-C_6H_4-$ | 4-CN | $-CH(C_2H_5)-CH_2-$ | $-N(CH_3)_2$ |
| 143 | $4-OCH_3-C_6H_4-$ | H | $-CH(CH_3)-CH(CH_3)-$ | $-N(CH_3)_2$ |
| 144 | $4-OCH_3-C_6H_4-$ | H | $-CH_2-CH(CH_3)-$ | $-N(C_2H_5)_2$ |
| 145 | $4-OCH_3-C_6H_4-$ | 4-Cl | $-CH(CH_3)-CH_2-$ | $-NHC_3H_7(i)$ |
| 146 | $4-OCH_3-C_6H_4-$ | 2-Cl | $-(CH_2)_3-CH(CH_3)-$ | $-N(C_2H_5)_2$ |
| 147 | 2-thienyl | H | $-CH(CH_3)-CH_2-$ | $-N(CH_3)_2$ |
| 148 | 2-thienyl | H | $-CH_2-CH(CH_3)-$ | $-N(CH_3)_2$ |
| 149 | 5-methyl-2-thienyl | H | $-CH(CH_3)-CH_2-$ | $-N(C_2H_5)_2$ |
| 150 | 5-methyl-2-thienyl | 4-CN | $-CH_2-CH(CH_3)-$ | $-N(C_2H_5)_2$ |
| 151 | α-Naphthyl | H | $-CH(CH_3)-CH_2-$ | $-N(C_2H_5)_2$ |
| 152 | β-Naphthyl | H | $-(CH_2)_2-$ | $-N(CH_3)_2$ |
| 153 | $C_6H_5-$ | H | $-(CH_2)_4-$ | $-N(C_2H_5)_2$ |
| 154 | $4-F-C_6H_4-$ | H | $-(CH_2)_4-$ | $-N(C_2H_5)_2$ |
| 155 | $4-OCH_3-C_6H_4-$ | H | $-(CH_2)_4-$ | $-N(C_2H_5)_2$ |
| 156 | $4-Cl-C_6H_4-$ | H | $-(CH_2)_4-$ | $-N(C_2H_5)_2$ |
| 157 | $2-F-4-F-C_6H_3-$ | H | $-(CH_2)_4-$ | $-N(C_2H_5)_2$ |

-continued

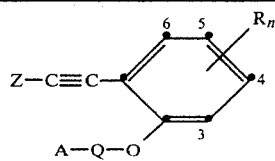

| No. | Z | $R_n$ | Q | A | Physical data |
|-----|---|-------|---|---|---------------|
| 201 | $C_6H_5-$ | H | $-(CH_2)_2-$ | $-N(C_2H_5)_2$ | $n_D^{25}$: 1.5988 |
| 202 | $C_6H_5-$ | H | $-(CH_2)_3-$ | $-N(C_2H_5)_2$ | |
| 203 | $C_6H_5-$ | 5-$NO_2$ | $-(CH_2)_2-$ | $-N(C_2H_5)_2$ | |
| 204 | $C_6H_5-$ | 3-$NO_2$ | $-(CH_2)_2-$ | $-N(C_2H_5)_2$ | |
| 205 | $C_6H_5-$ | 5-Cl | $-(CH_2)_2-$ | $-N(C_2H_5)_2$ | |
| 206 | $C_6H_5-$ | 3-Cl | $-(CH_2)_2-$ | $-NHC_2H_5$ | |
| 207 | $C_6H_5-$ | 5-CN | $-(CH_2)_2-$ | $-N(C_2H_5)_2$ | |
| 208 | $C_6H_5-$ | 3-CN | $-(CH_2)_2-$ | $-N(C_2H_5)_2$ | |
| 209 | $C_6H_5-$ | 3-$NO_2$ | $-(CH_2)_3-$ | $-N(C_2H_5)_2$ | |
| 210 | 4-$CF_3$—2-Cl—$C_6H_3-$ | H | $-(CH_2)_2-$ | $-N(nC_3H_7)_2$ | |
| 211 | 4-$CF_3$—2-Cl—$C_6H_3-$ | 5-CN | $-(CH_2)_2-$ | $-N(C_2H_5)_2$ | |
| 212 | 3-$CH_3$—5-$CH_3$—$C_6H_3-$ | H | $-(CH_2)_2-$ | $-N(C_2H_5)_2$ | |
| 213 | 4-$iC_3H_7$—$C_6H_4-$ | H | $-(CH_2)_2-$ | $-N(C_2H_5)_2$ | |
| 214 | 4-$iC_3H_7$—$C_6H_4-$ | H | $-(CH_2)_2-$ | $-N(nC_4H_9)_2$ | |
| 215 | 4-CN—$C_6H_4-$ | H | $-(CH_2)_2-$ | $-N(C_2H_5)_2$ | |
| 216 | 4-CN—$C_6H_4-$ | 3-Cl | $-(CH_2)_2-$ | $-N(C_2H_5)_2$ | |
| 217 | 4-$NO_2$—$C_6H_4-$ | H | $-(CH_2)_2-$ | $-N(C_2H_5)_2$ | |
| 218 | 2-$C_2H_5$—6-$CH_3$—$C_6H_3-$ | H | $-(CH_2)_2-$ | $-N(C_2H_5)_2$ | |
| 219 | 2-$C_2H_5$—6-$CH_3$—$C_6H_3-$ | 3-$NO_2$ | $-(CH_2)_2-$ | $-N(OCH_3)CH_3$ | |
| 220 | 4-$OCH_3$—$C_6H_4-$ | H | $-(CH_2)_2-$ | $-N(C_2H_5)_2$ | |
| 221 | 4-$SC_2H_5$—$C_6H_4-$ | H | $-(CH_2)_3-$ | $-N(nC_3H_7)_2$ | |
| 222 | 4-$SC_2H_5$—$C_6H_4-$ | 5-$NO_2$ | $-(CH_2)_2-$ | $-N(C_2H_5)_2$ | |
| 223 | 3-$OCH_3$—$C_6H_4-$ | H | $-(CH_2)_2-$ | $-N(C_2H_5)_2$ | |
| 224 | thienyl (2-) | H | $-(CH_2)_2-$ | $-N(C_2H_5)_2$ | |
| 225 | thienyl (3-) | H | $-(CH_2)_2-$ | $-N(C_2H_5)_2$ | |
| 226 | 5-methylthienyl (2-) | H | $-(CH_2)_3-$ | $-N(C_2H_5)_2$ | |
| 227 | 5-methylthienyl (2-) | H | $-(CH_2)_3-$ | $-N(C_2H_5)_2$ | |

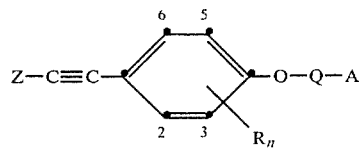

| No. | Z | $R_n$ | Q | A | Physical data (°C.) |
|-----|---|-------|---|---|---------------------|
| 401 | $C_6H_5-$ | H | $-(CH_2)_2-$ | $-N(C_2H_5)_2 \cdot HCl$ | |
| 402 | $C_6H_5-$ | H | $-(CH_2)_2-$ | $-N(C_2H_5)(CH_3)$ | $n_D^{25}$: 1.6203 |
| 403 | $C_6H_5-$ | H | $-(CH_2)_6-$ | $-N(C_2H_5)_2$ | |
| 404 | $C_6H_5-$ | H | $-(CH_2)_2-$ | $-NHC_2H_5$ | viscous |
| 405 | $C_6H_5-$ | H | $-(CH_2)_2-$ | $-N(CH_3)_2$ | m.p 34–36° |

-continued

| No. | | | | | |
|---|---|---|---|---|---|
| 406 | C₆H₅— | H | —(CH₂)₂— | 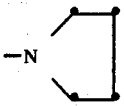 | viscous |
| 407 | C₆H₅— | 2-Cl, 5-Cl | —(CH₂)₂— | —N(C₂H₅)₂ | $n_D^{25}$: 1.6173 |
| 408 | C₆H₅— | H | —(CH₂)₃— | —N(C₂H₅)₂ | $n_D^{25}$: 1.5934 |
| 409 | C₆H₅— | H | —(CH₂)₂— | 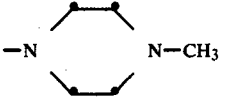 | m.p. 65–70° |
| 410 | C₆H₅— | 3-Cl, 5-Cl | —(CH₂)₂— | —N(C₂H₅)₂ | |
| 411 | C₆H₅— | 2-CH₃, 5-CH₃ | —(CH₂)₂— | —N(C₂H₅)₂ | |
| 412 | C₆H₅— | 5-NO₂ | —(CH₂)₂— | —N(C₂H₅)₂ | |
| 413 | C₆H₅— | 2-Cl, 5-Cl | —(CH₂)₃— | —N(CH₃)₂ | |
| 414 | C₆H₅— | 2-Cl, 6-Cl | —(CH₂)₃— | —N(C₂H₅)₂ | |
| 415 | C₆H₅— | 5-NO₂ | —(CH₂)₃— | —N(C₂H₅)₂ | |
| 416 | 4-F—C₆H₄— | H | —(CH₂)₂— | —N(C₂H₅)₂ | b.p. 156–162°/ 0.08 mb |
| 417 | 4-Cl—C₆H₄— | H | —(CH₂)₃— | —N(C₂H₅)₂ | m.p. 69–70° |
| 418 | 4-CF₃—C₆H₄— | H | —(CH₂)₂— | —N(C₂H₅)₂ | |
| 419 | 4-SCH₃—C₆H₄— | H | —(CH₂)₂— | —N(C₂H₅)₂ | |
| 420 | 4-CF₃—2-Cl—C₆H₃— | 5-NO₂ | —(CH₂)₂— | —N(C₂H₅)₂ | |
| 421 | 4-CF₃—2-Cl—C₆H₃— | 5-NO₂ | —(CH₂)₃— | —N(C₂H₅)₂ | |
| 422 | 3-CH₃—5-CH₃—C₆H₃— | H | —(CH₂)₂— | —N(C₂H₅)₂ | $n_D^{20}$: 1.5880 |
| 423 | 4-iC₃H₇—C₆H₄— | H | —(CH₂)₂— | —N(C₂H₅)₂ | m.p. 50° |
| 424 | 4-iC₃H₇—C₆H₄— | 2-Cl, 5-Cl | —(CH₂)₃— | —N(C₂H₅)₂ | |
| 425 | 4-CN—C₆H₄— | H | —(CH₂)₂— | —N(C₂H₅)₂ | |
| 426 | 4-CN—C₆H₄— | 3-Cl, 5-Cl | —(CH₂)₂— | —N(C₂H₅)₂ | |
| 427 | 4-NO₂—C₆H₄— | H | —(CH₂)₂— | —N(C₂H₅)₂ | m.p. 58° |
| 428 | 3-NO₂—C₆H₄— | H | —(CH₂)₂— | —N(C₂H₅)₂ | $n_D^{30}$: 1.5980 |
| 429 | 2-NO₂—4-Cl—C₆H₃— | H | —(CH₂)₂— | —N(C₂H₅)₂ | |
| 430 | 2-NO₂—4-Cl—C₆H₃— | 2-CH₃, 5-CH₃ | —(CH₂)₂— | —N(C₂H₅)₂ | |
| 431 | 2-C₂H₅—6-CH₃—C₆H₃— | H | —(CH₂)₂— | —N(C₂H₅)₂ | $n_D^{30}$: 1.5820 |
| 432 | C₆F₅— | H | —(CH₂)₂— | —N(C₂H₅)₂ | m.p. 65° |
| 433 | 4-OCH₃—C₆H₄— | H | —(CH₂)₂— | —N(C₂H₅)₂ | m.p. 59–60° |
| 434 | 4-OCH₃—C₆H₄— | H | —(CH₂)₂— | —N(C₂H₅)(CH₃) | m.p. 40–45° |
| 435 | 4-SC₂H₅—C₆H₄— | H | —(CH₂)₂— | —N(C₂H₅)₂ | |
| 436 | 3-CH₃—5-OH—C₆H₃— | H | —(CH₂)₂— | —N(C₂H₅)₂ | oil |
| 437 | 3-CF₃—C₆H₄— | H | —(CH₂)₂— | —N(nC₃H₇)₂ | |
| 438 | 3-CF₃—C₆H₄— | H | —(CH₂)₄— | —N(C₂H₅)₂ | |
| 439 | 3-CF₃—5-CF₃—C₆H₃— | H | —(CH₂)₂— | —N(C₂H₅)₂ | |
| 440 | 3-CF₃—5-CF₃—C₆H₃— | H | —(CH₂)₂— | —N(OCH₃)CH₃ | |
| 441 | 3-H₂N—CO—C₆H₄— | H | —(CH₂)₂— | —N(C₂H₅)₂ | m.p. 133° |
| 442 | 3-CN—C₆H₄— | H | —(CH₂)₂— | —N(C₂H₅)₂ | |
| 443 | 3-COOCH₃—C₆H₄— | H | —(CH₂)₂— | —N(C₂H₅)₂ | |
| 444 | 3-COOCH₃—C₆H₄— | 3-Cl, 5-Cl | —(CH₂)₂— | —N(C₂H₅)₂ | |
| 445 | 2-OCH₃—C₆H₄— | H | —(CH₂)₂— | —N(CH₃)₂ | oil |
| 446 | 3-OCH₃—C₆H₄— | 2-CH₃, 5-CH₃ | —(CH₂)₃— | —N(CH₃)₂ | |
| 447 | 3-CON(CH₃)₂—C₆H₄— | H | —(CH₂)₂— | —N(C₂H₅)₂ | |
| 448 | 3-COSC₂H₅—C₆H₄— | H | —(CH₂)₂— | —N(C₂H₅)₂ | |
| 449 | 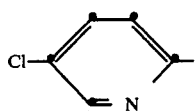 | H | —(CH₂)₂— | —N(C₂H₅)₂ | |
| 450 | 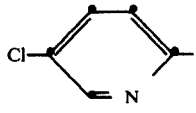 | H | —(CH₂)₃— | —N(C₂H₅)₂ | |

| | | | | | |
|---|---|---|---|---|---|
| 451 | 3,4-diCl-pyridyl | 5-NO$_2$ | —(CH$_2$)$_3$— | —N(C$_2$H$_5$)$_2$ | |
| 452 | 3,4-diCl-pyridyl | H | —(CH$_2$)$_2$— | —N(C$_2$H$_5$)$_2$ | m.p. 58° |
| 453 | 3-CF$_3$-pyridyl | H | —(CH$_2$)$_2$— | —N(C$_2$H$_5$)$_2$ | |
| 454 | 3-CF$_3$-pyridyl | H | —(CH$_2$)$_2$— | —N(pyrrolidinyl) | |
| 455 | 3-CF$_3$-4-Cl-pyridyl | H | —(CH$_2$)$_2$— | —N(C$_2$H$_5$)$_2$ | |
| 456 | pyridyl | H | —(CH$_2$)$_2$— | —N(C$_2$H$_5$)$_2$ | $n_D^{30}$: 1.6040 |
| 457 | 3-I-pyridyl | H | —(CH$_2$)$_2$— | —N(C$_2$H$_5$)$_2$ | |
| 458 | 3-I-pyridyl | 2-Cl, 6-Cl | —(CH$_2$)$_2$— | —N(C$_2$H$_5$)$_2$ | |
| 459 | 4-CN-3-Cl-pyridyl | H | —(CH$_2$)$_2$— | —N(C$_2$H$_5$)$_2$ | |
| 460 | 4-CN-3-Cl-pyridyl | H | —(CH$_2$)$_3$— | —N(C$_2$H$_5$)$_2$ | |
| 461 | 3-CN-pyridyl | 3-Cl, 5-Cl | —(CH$_2$)$_2$— | —N(C$_2$H$_5$)$_2$ | |
| 462 | 3-CN-pyridyl | H | —(CH$_2$)$_2$— | —N(C$_2$H$_5$)$_2$ | |

-continued
| | | | | | |
|---|---|---|---|---|---|
| 463 | 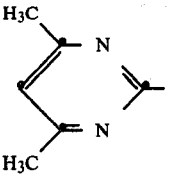 | H | —(CH$_2$)$_2$— | —N(C$_2$H$_5$)$_2$ | |
| 464 | 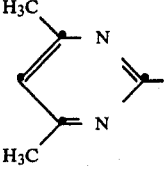 | H | —(CH$_2$)$_3$— | —N(OCH$_3$)CH$_3$ | |
| 465 | 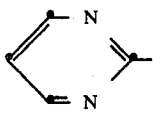 | H | —(CH$_2$)$_2$— | —N(C$_2$H$_5$)$_2$ | |
| 466 | 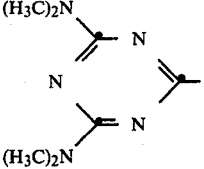 | H | —(CH$_2$)$_2$— | —N(C$_2$H$_5$)$_2$ | |
| 467 | 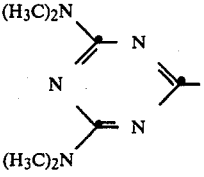 | H | —(CH$_2$)$_2$— | —N(CH$_3$)$_2$ | |
| 468 | 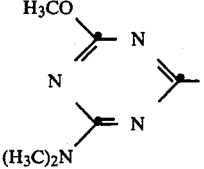 | H | —(CH$_2$)$_2$— | —N(C$_2$H$_5$)$_2$ | |
| 469 | 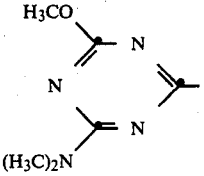 | H | —(CH$_2$)$_3$— | —N(C$_2$H$_5$)$_2$ | |
| 470 | 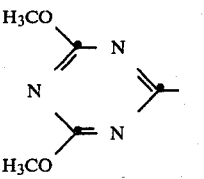 | H | —(CH$_2$)$_3$— | —N(C$_2$H$_5$)$_2$ | |
| 471 | 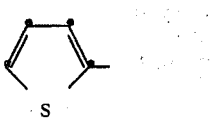 | H | —(CH$_2$)$_2$— | —N(C$_2$H$_5$)$_2$ | n$_D^{30}$: 1.6170 |
| 472 | 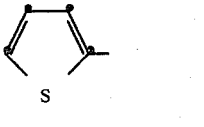 | 2-Cl, 5-Cl | —(CH$_2$)$_2$— | —N(C$_2$H$_5$)$_2$ | |

-continued

| No. | Ar | R | Alkylene | Amine | Notes |
|---|---|---|---|---|---|
| 473 | 5-methyl-2-thienyl | H | —(CH$_2$)$_2$— | —N(C$_2$H$_5$)$_2$ | |
| 474 | 5-methyl-2-thienyl | H | —(CH$_2$)$_3$— | —N(C$_2$H$_5$)$_2$ | |
| 475 | 3-(trifluoromethyl)-1,2,4-thiadiazol-5-yl (F$_3$C—, N—N, S ring) | H | —(CH$_2$)$_2$— | —N(C$_2$H$_5$)$_2$ | |
| 476 | 3-(trifluoromethyl)-1,2,4-thiadiazol-5-yl | H | —(CH$_2$)$_2$— | —N(OCH$_3$)CH$_3$ | |
| 477 | 2-furyl | H | —(CH$_2$)$_2$— | —N(C$_2$H$_5$)$_2$ | |
| 478 | 2-furyl | 2-Cl, 6-Cl | —(CH$_2$)$_3$— | piperidino (—N⟨ring⟩) | |
| 479 | 2-thiazolyl | H | —(CH$_2$)$_2$— | —N(C$_2$H$_5$)$_2$ | |
| 480 | 2-thiazolyl | 2-CH$_3$, 5-CH$_3$ | —(CH$_2$)$_2$— | —N(C$_2$H$_5$)$_2$ | |
| 481 | 2-oxazolyl | H | —(CH$_2$)$_2$— | —N(C$_2$H$_5$)$_2$ | |
| 482 | α-naphthyl | H | —(CH$_2$)$_2$— | —N(C$_2$H$_5$)$_2$ | $n_D^{30}$: 1.6310 |
| 483 | α-naphthyl | 2-CH$_3$, 5-CH$_3$ | —(CH$_2$)$_2$— | —N(C$_2$H$_5$)$_2$ | |
| 484 | α-naphthyl | H | —(CH$_2$)$_3$— | —N(C$_2$H$_5$)$_2$ | |
| 485 | β-naphthyl | H | —(CH$_2$)$_3$— | —N(C$_2$H$_5$)$_2$ | |
| 486 | β-naphthyl | 5-NO$_2$ | —(CH$_2$)$_3$— | —N(C$_2$H$_5$)$_2$ | |
| 487 | 2-pyridyl | H | —(CH$_2$)$_2$— | —N(C$_2$H$_5$)$_2$ | |
| 488 | C$_6$H$_5$— | H | —(CH$_2$)$_2$— | —N(C$_2$H$_5$)—CH$_2$—COOC$_2$H$_5$ | wax |
| 489 | C$_6$H$_5$— | H | —(CH$_2$)$_2$— | —N(C$_2$H$_5$)—CH$_2$—COOH | |
| 490 | C$_6$H$_5$— | H | —(CH$_2$)$_2$— | —N(CH$_2$—COOCH$_3$)$_2$ | |
| 491 | C$_6$H$_5$— | H | —(CH$_2$)$_2$— | —N(C$_2$H$_5$)—CH$_2$—CH$_2$OH | |
| 492 | C$_6$H$_5$— | H | —CH(CH$_3$)—CH$_2$— | —N(CH$_3$)$_2$ | $n_D^{25}$: 1.6091 |
| 493 | C$_6$H$_5$— | H | —CH$_2$—CH(CH$_3$)— | —N(CH$_3$)$_2$ | $n_D^{25}$: 1.6122 |

| | | | | |
|---|---|---|---|---|
| 494 | C$_6$H$_5$— | H | —CH—CH$_2$—<br>　│<br>　C$_2$H$_5$ | —N(CH$_3$)$_2$ |
| 495 | C$_6$H$_5$— | H | —CH—CH$_2$—<br>　│<br>　CH$_3$ | —N(C$_2$H$_5$)$_2$ |
| 496 | C$_6$H$_5$— | H | —CH—CH$_2$—<br>　│<br>　CH$_3$ | —N—C$_2$H$_5$<br>　│<br>　CH$_3$ |
| 497 | C$_6$H$_5$— | H | —CH—(CH$_2$)$_4$—<br>　│<br>　CH$_3$ | —N(CH$_3$)$_2$ |
| 498 | C$_6$H$_5$— | H | —CH$_2$—CH—<br>　　　　│<br>　　　　CH$_3$ | —N(C$_2$H$_5$)$_2$ |
| 499 | C$_6$H$_5$— | H | —CH$_2$—CH—<br>　　　　│<br>　　　　C$_2$H$_5$ | —N(CH$_3$)$_2$ |
| 500 | C$_6$H$_5$— | H | —CH—CH$_2$—CH—<br>　│　　　　　│<br>　CH$_3$　　　CH$_3$ | —N(CH$_2$—CH=CH$_2$)$_2$ |
| 501 | C$_6$H$_5$— | H | —CH—CH—<br>　│　　│<br>　CH$_3$　CH$_3$ | —N—C$_2$H$_5$<br>　│<br>　CH$_3$ |
| 502 | C$_6$H$_5$— | 2-Cl | —CH—CH$_2$—<br>　│<br>　CH$_3$ | —N—C$_4$H$_9$(n)<br>　│<br>　CH$_3$ |
| 503 | C$_6$H$_5$— | 5-CH$_3$ | —CH—CH$_2$—<br>　│<br>　CH$_3$ | —N(CH$_3$)$_2$ |
| 504 | C$_6$H$_5$— | 5-CH$_3$ | —CH$_2$—CH—<br>　　　　│<br>　　　　CH$_3$ | —N(C$_2$H$_5$)$_2$ |
| 505 | 4-F—C$_6$H$_4$— | H | —CH—CH$_2$—<br>　│<br>　CH$_3$ | —N(CH$_3$)$_2$ |
| 506 | 4-F—C$_6$H$_4$— | H | —CH—CH$_2$—<br>　│<br>　CH$_3$ | —N(C$_2$H$_5$)$_2$ |
| 507 | 4-F—C$_6$H$_4$— | H | —CH—CH$_2$—<br>　│<br>　C$_2$H$_5$ | —N(CH$_3$)$_2$ |
| 508 | 4-F—C$_6$H$_4$— | H | —CH$_2$—CH—<br>　　　　│<br>　　　　CH$_3$ | —N(CH$_3$)$_2$ |
| 509 | 4-F—C$_6$H$_4$— | H | —(CH$_2$)$_2$—CH—<br>　　　　　│<br>　　　　　CH$_3$ | —N—C$_2$H$_5$<br>　│<br>　CH$_3$ |
| 510 | 4-F—C$_6$H$_4$— | H | —CH$_2$—CH—CH$_2$—<br>　　　　│<br>　　　　CH$_3$ | —N(CH$_3$)$_2$ |
| 511 | 4-OCH$_3$—C$_6$H$_4$— | 5-CH$_3$ | —CH—CH$_2$—<br>　│<br>　C$_2$H$_5$ | —N(CH$_3$)$_2$ |
| 512 | 4-OCH$_3$—C$_6$H$_4$— | H | —CH—CH$_2$—<br>　│<br>　CH$_3$ | —N(CH$_3$)$_2$ |

-continued

| No. | | | | |
|---|---|---|---|---|
| 513 | 4-OCH$_3$—C$_6$H$_4$— | H | —CH—(CH$_2$)$_2$—<br>\|<br>CH$_3$ | —N⟨azetidine⟩ |
| 514 | 4-OCH$_3$—C$_6$H$_4$— | 2-Cl | —(CH$_2$)$_3$—CH—<br>\|<br>CH$_3$ | —N(CH$_3$)$_2$ |
| 515 | 4-OCH$_3$—C$_6$H$_4$— | H | —CH$_2$—CH—CH$_2$—<br>\|<br>CH$_3$ | —N(C$_2$H$_5$)$_2$ |
| 516 | 4-OCH$_3$—C$_6$H$_4$— | H | —CH—CH—<br>\|  \|<br>CH$_3$ CH$_3$ | —N(CH$_3$)$_2$ |
| 517 | 4-OCH$_3$—C$_6$H$_4$— | H | —CH—CH$_2$—<br>\|<br>C$_2$H$_5$ | —N(C$_2$H$_5$)$_2$ |
| 518 | 2-thienyl | H | —CH—CH$_2$—<br>\|<br>CH$_3$ | —N(CH$_3$)$_2$ |
| 519 | 2-thienyl | H | —CH$_2$—CH—<br>\|<br>CH$_3$ | —N(CH$_3$)$_2$ |
| 520 | 2-thienyl | H | —CH$_2$—CH—<br>\|<br>C$_2$H$_5$ | —N—C$_2$H$_5$<br>\|<br>CH$_3$ |
| 521 | 2-thienyl | H | —CH—(CH$_2$)$_2$—<br>\|<br>CH$_3$ | —N(C$_3$H$_7$—n)$_2$ |
| 522 | 5-methyl-2-thienyl | 5-CH$_3$ | —CH$_2$—CH—CH$_2$—<br>\|<br>CH$_3$ | —NHC$_4$H$_9$(n) |
| 523 | 5-methyl-2-thienyl | H | —CH—CH$_2$—<br>\|<br>CH$_3$ | —N(C$_2$H$_5$)$_2$ |
| 524 | 2-thienyl | 2-Cl | —CH—CH$_2$—<br>\|<br>C$_2$H$_5$ | —N(CH$_3$)$_2$ |
| 525 | α-Naphthyl | H | —CH—CH$_2$—<br>\|<br>C$_2$H$_5$ | —N⟨pyrrolidinyl⟩ |
| 526 | α-naphthyl | H | —CH$_2$—CH—<br>\|<br>CH$_3$ | —N(CH$_3$)$_2$ |
| 527 | β-naphthyl | 5-CH$_3$ | —CH$_2$—CH—<br>\|<br>CH$_3$ | —N(CH$_3$)$_2$ |

-continued

| | | | | | |
|---|---|---|---|---|---|
| 528 | β-naphthyl | H | —CH—CH—<br>     |    |<br>   CH₃ CH₃ | —N(C₂H₅)₂ | |
| 529 | 4-C₂H₅—O—CO—NH—C₆H₄— | H | —(CH₂)₂— | —N(C₂H₅)₂ | m.p. 92° |
| 530 | 4-CF₃—CO—NH—C₆H₄— | H | —(CH₂)₂— | —N(C₂H₅)₂ | m.p. 140° |
| 531 | 4-C₃H₇—i-CO—NH—C₆H₄— | H | —(CH₂)₂— | —N(C₂H₅)₂ | m.p. 147° |
| 532 | 4-CH₃—O—CO—NH—C₆H₄— | H | —(CH₂)₂— | —N(C₂H₅)₂ | m.p. 84° |
| 533 | 3-(CH₃)₂N—CH=N—C₆H₄— | H | —(CH₂)₂— | —N(C₂H₅)₂ | m.p. 37–38° |
| 534 | 3-N₃—C₆H₄— | H | —(CH₂)₂— | —N(C₂H₅)₂ | |
| 535 | 4-N₃—C₆H₄— | H | —(CH₂)₂— | —N(C₂H₅)₂ | |
| 536 | 4-(C₂H₅)₂N—SO₂—C₆H₄— | H | —(CH₂)₂— | —N(C₂H₅)₂ | |
| 537 | 4-(CH₃)₂N—C₆H₄— | H | —(CH₂)₂— | —N(C₂H₅)₂ | |
| 538 | 4-CH₃—O—CH₂—C₆H₄— | H | —(CH₂)₂— | —N(C₂H₅)₂ | |
| 539 | 4-CN—CH₂—C₆H₄— | H | —(CH₂)₂— | —N(C₂H₅)₂ | |
| 540 | 4-HOOC—(CH₂)₂—C₆H₄— | H | —(CH₂)₂— | —N(C₂H₅)₂ | |
| 541 | 4-C₂H₅—NH—C₆H₄— | H | —(CH₂)₂— | —N(C₂H₅)₂ | |
| 542 | 4-Cl—CH₂—C₆H₄— | H | —(CH₂)₂— | —N(C₂H₅)₂ | |
| 543 | 4-CH₃—O—CO—C₆H₄— | H | —(CH₂)₂— | —N(C₂H₅)₂ | |
| 544 | 4-SCH₃—C₆H₄— | H | —(CH₂)₂— | —N(C₂H₅)₂ | |
| 545 | 4-CH₂F—O—C₆H₄— | H | —(CH₂)₂— | —N(C₂H₅)₂ | |
| 546 | 3-OCH₃—C₆H₄— | H | —(CH₂)₂— | —N(C₂H₅)₂ | |
| 547 | 3-(CH₃)₂N—C₆H₄— | H | —(CH₂)₂— | —N(C₂H₅)₂ | |
| 548 | 3-C₂H₅—O—CO—NH—C₆H₄— | H | —(CH₂)₂— | —N(C₂H₅)₂ | |
| 549 | 3-C₂H₅—NH—C₆H₄— | H | —(CH₂)₂— | —N(C₂H₅)₂ | |
| 550 | C₆H₅— | H | —(CH₂)₄— | —N(C₂H₅)₂ | |
| 551 | 4-F—C₆H₄— | H | —(CH₂)₄— | —N(C₂H₅)₂ | |
| 552 | 4-OCH₃—C₆H₄— | H | —(CH₂)₄— | —N(C₂H₅)₂ | |
| 553 | 4-Cl—C₆H₄— | H | —(CH₂)₄— | —N(C₂H₅)₂ | |
| 554 | 4-NH₂—C₆H₄— | H | —(CH₂)₂— | —N(C₂H₅)₂ | m.p. 103° |
| 555 | 3-NH₂—C₆H₄— | H | —(CH₂)₂— | —N(C₂H₅)₂ | m.p. 51° |
| 556 | 2-NH₂—C₆H₄— | H | —(CH₂)₂— | —N(C₂H₅)₂ | |
| 557 | 4-NH₂—C₆H₄— | H | —CH—CH₂—<br>     |<br>   CH₃ | —N(C₂H₅)₂ | |
| 558 | 4-OH—C₆H₄— | H | —(CH₂)₂— | —N(C₂H₅)₂ | |
| 559 | 3-OH—C₆H₄— | H | —(CH₂)₂— | —N(C₂H₅)₂ | |
| 560 | 2-OH—C₆H₄— | H | —(CH₂)₂— | —N(C₂H₅)₂ | |
| 561 | 4-OH—C₆H₄— | 3-NO₂ | —(CH₂)₂— | —N(C₂H₅)₂ | |
| 562 | 4-C₂H₅—O—C₆H₄— | H | —(CH₂)₂— | —N(C₂H₅)₂ | |
| 563 | 3-C₂H₅—O—C₆H₄— | H | —(CH₂)₂— | —N(C₂H₅)₂ | |
| 564 | 4-C₂H₅—O—C₆H₄— | 3-NO₂ | —(CH₂)₂ | —N(C₂H₅)₂ | |
| 565 | 4-C₂H₅—O—C₆H₄ | H | —CH—CH₂<br>     |<br>   CH₃ | —N(CH₃)₂ | |
| 566 | 4-CN—C₆H₄— | 3-NO₂ | —CH—CH₂—<br>     |<br>   CH₃ | —N(CH₃)₂ | |
| 567 | 4-CN—C₆H₄— | H | —CH—CH₂—<br>     |<br>   CH₃ | —N(CH₃)₂ | |
| 568 | 3-CN—C₆H₄— | H | —CH—CH₂—<br>     |<br>   CH₃ | —N(CH₃)₂ | |
| 569 | 3-CN—C₆H₄— | 3-NO₂ | —CH—CH₂—<br>     |<br>   CH₃ | —N(CH₃)₂ | |
| 570 | 4-NaO—CO—C₆H₄— | H | —CH—CH₂—<br>     |<br>   CH₃ | —N(CH₃)₂ | |
| 571 | 4-NaO—CO—C₆H₄— | H | —(CH₂)₂— | —N(C₂H₅)₂ | |
| 572 | 3-NaO—CO—C₆H₄— | H | —(CH₂)₂— | —N(C₂H₅)₂ | |
| 573 | 4-OH—NH—C₆H₄— | H | —(CH₂)₂— | —N(C₂H₅)₂ | |
| 574 | 3-OH—NH—C₆H₄— | H | —(CH₂)₂— | —N(C₂H₅)₂ | |
| 575 | 4-NH₂—NH—C₆H₄— | H | —(CH₂)₂— | —N(C₂H₅)₂ | |
| 576 | 3-NH₂—NH—C₆H₄— | H | —(CH₂)₂— | —N(C₂H₅)₂ | |
| 577 | 4-NH₂—NH—C₆H₄— | H | —CH—CH₂—<br>     |<br>   CH₃ | —N(CH₃)₂ | |

-continued
| | | | | |
|---|---|---|---|---|
| 578 | 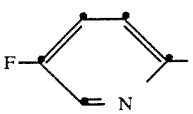 | H | —(CH$_2$)$_2$— | —N(C$_2$H$_5$)$_2$ |
| 579 | 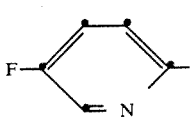 | H | —CH—CH$_2$—<br>\|<br>CH$_3$ | —N(CH$_3$)$_2$ |
| 580 | 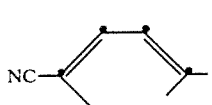 | H | —CH—CH$_2$—<br>\|<br>CH$_3$ | —N(CH$_3$)$_2$ |
| 581 | 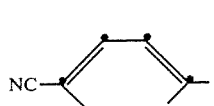 | H | —(CH$_2$)$_2$— | —N—C$_2$H$_5$<br>\|<br>CH$_3$ |
| 582 | 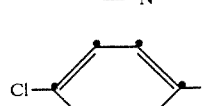 | H | —CH(CH$_3$)— | —N(C$_2$H$_5$)$_2$ |
| 583 | 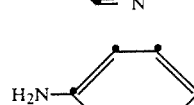 | H | —(CH$_2$)$_2$— | —N(C$_2$H$_5$)$_2$ |
| 584 | 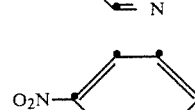 | H | —(CH$_2$)$_2$— | —N(C$_2$H$_5$)$_2$ |
| 585 | 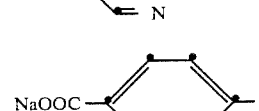 | H | —(CH$_2$)$_2$— | —N(C$_2$H$_5$)$_2$ |
| 586 | 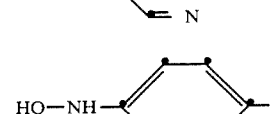 | H | —(CH$_2$)$_2$— | —N(C$_2$H$_5$)$_2$ |
| 587 | 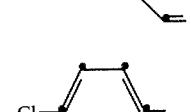 | H | —(CH$_2$)$_2$— | —N(C$_2$H$_5$)$_2$ |
| 588 | 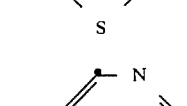 | H | —(CH$_2$)$_2$— | —N(C$_2$H$_5$)$_2$ |
| 589 | 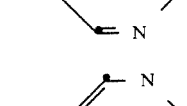 | H | —(CH$_2$)$_2$— | —N(C$_2$H$_5$)$_2$ |
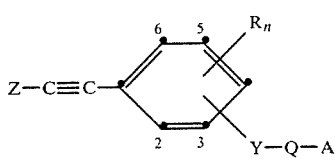

| No. | Z | $R_n$ | —Y—Q—A |
|---|---|---|---|
| 701 | $C_6H_5$— | H | 4-NH—$(CH_2)_2$—$N(C_2H_5)_2$ |
| 702 | $C_6H_5$— | H | 4-N($CH_3$)—$(CH_2)_2$—$N(C_2H_5)_2$ |
| 703 | $C_6H_5$— | H | 3-NH—$(CH_2)_2$—$N(C_2H_5)_2$ |
| 704 | $C_6H_5$— | H | 3-N($CH_3$)—$(CH_2)_2$—$N(C_2H_5)_2$ |
| 705 | $C_6H_5$— | H | 2-NH—$(CH_2)_2$—$N(C_2H_5)_2$ |
| 706 | $C_6H_5$— | H | 2-N($CH_3$)—$(CH_2)_2$—$N(C_2H_5)_2$ |
| 707 | $C_6H_5$— | H | 2-S—$(CH_2)_2$—$N(C_2H_5)_2$ |
| 708 | $C_6H_5$— | H | 3-S—$(CH_2)_2$—$N(C_2H_5)_2$ |
| 709 | $C_6H_5$— | H | 4-S—$(CH_2)_2$—$N(C_2H_5)_2$ |

FORMULATION EXAMPLES

EXAMPLE 6

Formulation Examples for liquid active ingredients of the formula I (throughout, percentages are by weight)

| (a) Emulsifiable concentrates | (a) | (b) | (c) |
|---|---|---|---|
| active ingredient | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexane | — | 15% | 20% |
| xylene mixture | 70% | 25% | 20% |

Emulsions of any required concentration can be produced from such concentrates by dilution with water.

| (b) Solutions | (a) | (b) | (c) | (d) |
|---|---|---|---|---|
| active ingredient | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| ligroin (boiling range 160–190°) | — | — | 94% | — |

These solutions are suitable for application in the form of microdrops.

| (c) Granulates | (a) | (b) |
|---|---|---|
| active ingredient | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| (d) Dusts | (a) | (b) |
|---|---|---|
| active ingredient | 2% | 5% |
| highly dispersed silicic acid | 1% | 5% |
| talcum | 97% | — |
| kaolin | — | 90% |

Dusts which are ready for use are obtained by intimately mixing the carriers with the active ingredient.

EXAMPLE 7

Formulation examples for solid active ingredients of the formula I (throughout, percentages are by weight)

| (a) Wettable powders | (a) | (b) |
|---|---|---|
| active ingredient | 20% | 60% |
| sodium lignosulfonate | 5% | 5% |
| sodium laurylsulfate | 3% | — |
| sodium diisobutylnaphthalene-sulfonate | — | 6% |
| octylphenol polyethylene glycol ether (7–8 moles of ethylene oxide) | — | 2% |
| highly dispersed silicic acid | 5% | 27% |
| kaolin | 67% | — |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | |
|---|---|
| active ingredient | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50%. |

Emulsions of any required concentration can be obtained from this concentrate by dilution with water.

| (c) Dusts | (a) | (b) |
|---|---|---|
| active ingredient | 5% | 8% |
| talcum | 95% | — |
| kaolin | — | 92% |

Dusts which are ready for use are obtained by mixing the active ingredient with the carriers, and grinding the mixture in a suitable mill.

| (d) Extruder granulate | |
|---|---|
| active ingredient | 10% |
| sodium lignosulfonate | 2% |
| carboxymethylcellulose | 1% |
| kaolin | 87%. |

The active ingredient is mixed and ground with the adjuvants, and the mixture is subsequently moistened with water. The mixture is extruded and then dried in a stream of air.

| (e) Coated granulate | |
| --- | --- |
| active ingredient | 3% |
| polyethylene glycol 200 | 3% |
| kaolin | 94%. |

The finely ground active ingredient is uniformly applied, in a mixer, to the kaolin moistened with polyethylene glycol. Non-dusty coated granulates are obtained in this manner.

| (f) Suspension concentrate | |
| --- | --- |
| active ingredient | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32%. |

The finely ground active ingredient is intimately mixed with the adjuvants, giving a suspension concentrate from which suspensions of any desired concentration can be obtained by dilution with water.

BIOLOGICAL EXAMPLES
EXAMPLE 8

Postemergence herbicidal action (contact herbicide)

Both monocot and dicot weeds are sprayed postemergence, in the 4- to 6-leaf stage, with an aqueous active ingredient dispersion at a rate of application of 4 kg a.i./ha, and then kept at 24°–26° C. and 45–60% relative humidity. The test is evaluated at least 15 days after treatment and the results are assessed in accordance with the following rating:

1 = plants totally withered
2–3 = very pronounced action
4–6 = medium action
7–8 = insignificant action
9 = no action (as untreated controls)

POSTEMERGENCE ACTION

Rate of application: 4 kg a.i./ha

| Compound | Setaria | Solanum | Sinapis | Stellaria |
| --- | --- | --- | --- | --- |
| 1 | 2 | 1 | 1 | 1 |
| 402 | 1 | 1 | 1 | 1 |
| 408 | 4 | 1 | 2 | 4 |
| 416 | 2 | 1 | 1 | 1 |
| 417 | 3 | 1 | 1 | 1 |
| 422 | 5 | 1 | 1 | 2 |
| 423 | 6 | 1 | 1 | 3 |
| 431 | 4 | 1 | 1 | 2 |
| 432 | 7 | 2 | 1 | 3 |
| 433 | 3 | 1 | 1 | 1 |
| 438 | 1 | 2 | 1 | 2 |
| 452 | 6 | 1 | 1 | 3 |
| 456 | 7 | 1 | 2 | 3 |
| 471 | 3 | 1 | 1 | 2 |
| 482 | 6 | 1 | 2 | 2 |
| 492 | 4 | 1 | 2 | 3 |
| 493 | 4 | 2 | 2 | 3 |

What is claimed is:
1. A phenylacetylene compound of the formula

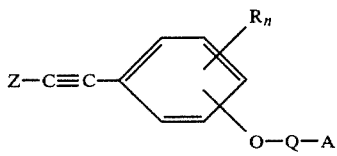

wherein
A is an amino group of the formula

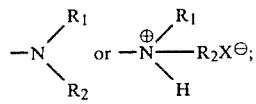

each of $R_1$ and $R_2$ is hydrogen; $C_3$–$C_6$alkenyl; $C_3$–$C_6$alkynyl; $C_3$–$C_8$cycloalkyl; or $C_1$–$C_6$alkyl optionally substituted by halogen, hydroxy, $C_1$–$C_4$alkoxy, alkoxycarbonyl containing at most 5 carbon atoms, cyano or carboxyl; or, together with the nitrogen atom to which they are attached, $R_1$ and $R_2$ form a 5- or 6-membered saturated heterocyclic ring system containing altogether at most 2 hetero-atoms and which is optionally substituted by $C_1$–$C_3$alkyl;
$X^\ominus$ is an anion;
R is hydrogen; nitro; cyano; trifluoromethyl; $C_1$–$C_4$alkoxy; $C_1$–$C_4$alkylthio; —$NR_5R_6$; CO—$NR_7R_8$; —$COOR_9$; —CO—$SR_{10}$; halogen; —$N_3$; or $C_1$–$C_4$alkyl optionally substituted by $C_1$–$C_4$alkyl, hydroxy, cyano or —$COOR_9$;
each of $R_5$, $R_7$, $R_8$, $R_9$ and $R_{10}$ is hydrogen; $C_1$–$C_6$alkyl; $C_3$–$C_8$alkenyl; or $C_3$–$C_8$alkynyl;
$R_6$ is hydrogen; $C_1$–$C_6$alkyl; $C_3$–$C_8$alkenyl; $C_3$–$C_8$alkynyl; —CO—$R_{11}$; —$COOR_{12}$; or —CO—$NHR_{13}$; in which $R_{11}$, $R_{12}$ and $R_{13}$ have the same meanings as $R_4$;
n is an integer from 1 to 4; and
Z is heterocyclic radical selected from the group consisting of furanyl, thienyl, pyridyl, pyrimidinyl, thiazolyl and triazinyl, each of which is optionally substituted by one or more radicals having the same meaning as R, formyl, —$SO_2$—$NR_7R_8$, —NH—$NH_2$, —NHOH, —SO—$R_9$, $SO_2$—$R_9$,

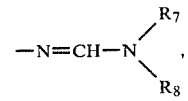

$COO^\ominus M^\oplus$ in which $M^\oplus$ is a sodium, potassium, calcium or magnesium cation, or $C_2$–$C_6$alkenyl which optionally substituted by nitro, cyano or —$COOR_9$.
2. A phenylacetylene compound according to claim 1, wherein the radical —O—Q—A is in the 4-position to the ethynyl radical.
3. A phenylacetylene compound according to claim 1, wherein the radical —O—Q—A is in the 3-position to the ethynyl radical.
4. A compound according to claim 1, wherein the direct alkylene bridge between the bridge member O and the nitrogen atom of the group A consists of 2 or 3 carbon atoms.

5. A compound according to claim 1, wherein the radical Z is furanyl or thienyl, each optionally substituted.

6. A compound according to claim 1, wherein the radical Z is pyridyl, pyrimidinyl, thiazolyl or triazinyl, each optionally substituted.

7. A compound according to claim 1, wherein $R_1$ and $R_2$ are methyl or ethyl.

8. A compound according to claim 1, wherein the radical —O—Q—A is in the 4-position to the ethynyl radical, the direct chain between the bridge member O and the nitrogen atom of the group A consists of 2 to 3 carbon atoms, the radical Z is furanyl or thienyl, each optionally substituted and $R_1$ and $R_2$ are methyl or ethyl.

9. A compound according to claim 1, wherein the radical —O—Q—A is in the 3-position to the ethynyl radical, the direct chain between the bridge member O and the nitrogen atom of the group A consists of 2 or 3 carbon atoms, the phenyl, radical Z is phenyl, furanyl or thienyl, each optionally substituted and $R_1$ and $R_2$ are methyl or ethyl.

10. A compound according to claim 1, wherein the radical —O—Q—A is in the 4-position to the ethynyl radical, the direct chain between the bridge member O and the nitrogen atom of the group A consists of 2 or 3 carbon atoms, the radical Z is pyridyl, pyrimidinyl, thiazolyl or triazinyl, each optionally substituted and $R_1$ and $R_2$ are methyl or ethyl.

11. A compound according to claim 1, wherein the radical —O—Q—A is in the 3-position to the ethynyl radical, the direct chain between the bridge member O and the nitrogen atom consists of 2 or 3 carbon atoms, the radical Z is pyridyl, pyrimidinyl, thiazolyl or triazinyl, each optionally substituted and $R_1$ and $R_2$ are methyl or ethyl.

12. A compound according to claims 8, 9, 10 or 11 in which

R is halogen, $C_1$-$C_4$alkyl, nitro or cyano, and n is 1.

13. 1-[4-(4-Methoxyphenylethynyl)phenoxy]-2-diethylaminoethane.

14. 1-[4-(4-Fluorophenylethynyl)phenoxy]-2-diethylaminoethane.

15. 1-[4-(2-Thienylethynyl)phenoxy]-2-diethylaminoethane according to claim 10.

16. A herbicidal composition comprising a herbicidally effective amount of at least one compound according to claim 1, 13 or 14, together with a suitable carrier therefor.

17. A method of controlling weeds, which method comprises applying thereto or to the locus thereof a herbicidally effective amount of a compound according to claim 1, 13 or 14.

18. A method according to claim 17 for selectively controlling weeds in crops of cultivated plants, which method comprises applying said compound postemergence.

19. A method according to claim 18, wherein the crop is cereals or maize.

* * * * *